(12) United States Patent
Gant et al.

(10) Patent No.: US 8,138,226 B2
(45) Date of Patent: Mar. 20, 2012

(54) SUBSTITUTED PHENETHYLAMINES WITH SEROTONINERGIC AND/OR NOREPINEPHRINERGIC ACTIVITY

(75) Inventors: Thomas G. Gant, Carlsbad, CA (US); Sepehr Sarshar, Cardiff by the Sea, CA (US)

(73) Assignee: Auspex Pharmaceuticals, La Jolla, CA (US)

( * ) Notice: Subject to any disclaimer, the term of this patent is extended or adjusted under 35 U.S.C. 154(b) by 658 days.

(21) Appl. No.: 12/234,318

(22) Filed: Sep. 19, 2008

(65) Prior Publication Data

US 2009/0023765 A1 Jan. 22, 2009

Related U.S. Application Data

(62) Division of application No. 11/565,451, filed on Nov. 30, 2006, now Pat. No. 7,456,317.

(60) Provisional application No. 60/741,315, filed on Dec. 1, 2005, provisional application No. 60/841,366, filed on Aug. 30, 2006.

(51) Int. Cl.
*A01N 33/02* (2006.01)
*A61K 31/135* (2006.01)

(52) U.S. Cl. .................................................. 514/650

(58) Field of Classification Search .................. None
See application file for complete search history.

(56) References Cited

U.S. PATENT DOCUMENTS

| | | | |
|---|---|---|---|
| 4,535,186 A | 8/1985 | Husbands | |
| 5,916,923 A * | 6/1999 | Rudolph et al. | 514/649 |
| 6,071,918 A * | 6/2000 | Cook | 514/321 |
| 6,221,335 B1 | 4/2001 | Foster | |
| 6,274,171 B1 | 8/2001 | Sherman | |
| 6,310,101 B1 | 10/2001 | Rudolph | |
| 6,395,788 B1 | 5/2002 | Iglehart, III | |
| 6,403,120 B1 | 6/2002 | Sherman | |
| 6,419,958 B2 | 7/2002 | Sherman | |
| 6,440,457 B1 | 8/2002 | Edgren | |
| 6,440,710 B1 | 8/2002 | Keinan et al. | |
| 6,444,708 B2 | 9/2002 | Rudolph | |
| 6,541,523 B2 | 4/2003 | Iglehart, III | |
| 6,579,899 B1 | 6/2003 | Wurtman | |
| 6,603,008 B1 | 8/2003 | Ando et al. | |
| 6,673,838 B2 | 1/2004 | Hadfield | |
| 6,924,393 B2 | 8/2005 | Dolitzky et al. | |
| 7,291,347 B2 | 11/2007 | Hadfield | |
| 7,456,317 B2 * | 11/2008 | Gant et al. | 564/305 |
| 7,517,990 B2 | 4/2009 | Ito et al. | |
| 2001/0046988 A1 | 11/2001 | Iglehart, III | |
| 2002/0013372 A1 | 1/2002 | Ekins | |
| 2002/0094995 A1 | 7/2002 | Foster | |
| 2003/0215507 A1 | 11/2003 | Sherman | |
| 2004/0029869 A1 | 2/2004 | Iglehart, III | |
| 2005/0054942 A1 | 3/2005 | Melker | |
| 2005/0118264 A1 | 6/2005 | Sela | |
| 2005/0181071 A1 | 8/2005 | Binder | |
| 2005/0233459 A1 | 10/2005 | Melker | |
| 2005/0261278 A1 | 11/2005 | Weiner | |
| 2007/0149622 A1 | 6/2007 | Gant et al. | |
| 2007/0197695 A1 | 8/2007 | Potyen et al. | |
| 2008/0033011 A1 | 2/2008 | Tung | |
| 2008/0234257 A1 | 9/2008 | Gant | |
| 2008/0280991 A1 | 11/2008 | Gant et al. | |
| 2008/0287774 A1 | 11/2008 | Katz-Brull | |
| 2009/0018207 A1 | 1/2009 | Gant | |
| 2009/0028873 A1 | 1/2009 | Gant et al. | |
| 2009/0069431 A1 | 3/2009 | Czarnik | |
| 2009/0076162 A1 | 3/2009 | Czarnik | |
| 2009/0312435 A1 | 12/2009 | Gant et al. | |
| 2010/0076087 A1 | 3/2010 | Gant et al. | |

FOREIGN PATENT DOCUMENTS

EP 0112669 A2 7/1984

(Continued)

OTHER PUBLICATIONS

Lessard et al., Influence of CYP2D6 activity on the disposition and cardiovascular toxicity of the antidepressant agent venlafaxine in humans, Pharmacogenetics 9:435-443 (1999).*

(Continued)

*Primary Examiner* — Johann Richter
*Assistant Examiner* — Thor Nielsen
(74) *Attorney, Agent, or Firm* — Dennis A. Bennett; Mike Sertic

(57) ABSTRACT

Chemical syntheses and medical uses of novel inhibitors of the uptake of monoamine neurotransmitters and pharmaceutically acceptable salts and prodrugs thereof, for the treatment and/or management of psychotropic disorders, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, and/or premature ejaculation are described.

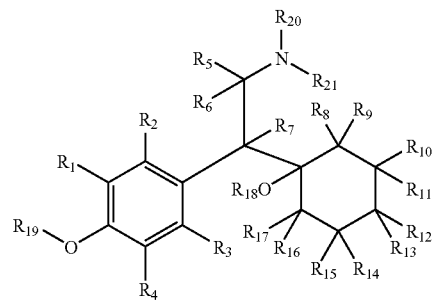

Formula 1

28 Claims, No Drawings

FOREIGN PATENT DOCUMENTS

| | | |
|---|---|---|
| EP | 0654264 B1 | 5/2001 |
| EP | 1202722 B1 | 7/2005 |
| WO | 9526325 A2 | 10/1995 |
| WO | 0112175 A1 | 2/2001 |
| WO | 0154681 A2 | 8/2001 |
| WO | 02085297 A2 | 10/2002 |
| WO | 2005112927 A1 | 12/2005 |
| WO | 2006034343 A2 | 3/2006 |
| WO | 2006044916 A2 | 4/2006 |
| WO | 2007064697 A1 | 6/2007 |
| WO | 2008140859 A1 | 11/2008 |
| WO | 2009018169 A1 | 2/2009 |
| WO | 2010028130 A2 | 3/2010 |
| WO | 2010120797 A2 | 10/2010 |
| WO | 2010120797 A3 | 10/2010 |

OTHER PUBLICATIONS

Kushner et al., Pharmacological uses and perspectives of heavy water and deuterated compounds, Can. J. Physiol. Pharmacol 77: 79-88 (1999).*

Yang et al., Synthesis of 3-Deuterated Diazepam and Nordiazepam 4-oxides and their use in the synthesis of other 3-Deuterated Derivatives, J Labelled Compounds Radiopharmaceuticals 38:753-759 (1996).*

Ettmayer et al., Lessons Learned from Marketed and Investigational Prodrugs, J. Medicinal Chem. 47: 2393-2404 (2004).*

Vippagunta et al., Crystalline solids, Advanced Drug Delivery Rev. 48: 3-26 (2001).*

Browne, TR et al.; Pharmacokinetic Equivalence of Stable-Isotope-Labeled and Unlabeled Drugs. Phenobarbital in Man; J Clin Pharmacol, 1982, 22, 309-315.

Dent, B.; Certificate of Analysis—Venlafaxine d6—HCI; BDG Synthesis XP-002489186, 2006.

Dent, B.; Certificate of Analysis—O-desmethylvenlafaxine d6; BDG Synthesis XP-002489187, 2006.

Lee, H. et. al.; Deuterium Magic Angle Spinning Studies of Substrates Bound to Cytochrome P450; Biochemistry 1999, 38, 10808-10813.

Basappa; Kavitha, C. V. et. al.; Simple and an efficient method for the synthesis of 1-[2-dimethylamino-1-(4-methoxyphenyl)-ethyl]-cyclohexanol hydrochloride: ( ) venlafaxine racemic mixtures; Bioorganic & Medicinal Chemistry Letters (2004), 14(12), 3279-3281.

Burm, AGL et. al.; Pharmacokinetics of Lidocaine and bupivacaine and stable isotope-labeled analogs: a study in healthy volunteers; Biopharmaceutics and Drug Disposition, 1988, 9, 85-95.

Kushner, D.J. et. al.; Pharmacological uses and perspectives of heavy water and deuterated compounds; Canadian Journal of Physiology and Pharmacology (1999), 77(2), 79-88.

Bauer, LA et. al.; Influence of long-term infusions on lidocaine kinetics; Clin. Pharmacol. Ther. 1982, 433-7.

Fisher, MB et. al.; The complexities inherent in attempts to decrease drug clearance by blocking sites of CCP-mediated metabolism; Curr Opin Drug Discov Develop; 2006, 9(1), 101-9.

Nelson, SD et. al.; The Use of Deuterium Isotope Effect to Probe the Active Site Properties, Mechanism of Cytochrome P450-catalyzed Reactions, and Mechanisms of Metabolically Dependent Toxicity; Drug Metabolism and Disposition 31:1481-1498, 2003.

Mamada, K. et. al.; Pharmacokinetic Equivalence of Deuterium-Labeled and Unlabeled Phenytoin; Drug Metabolism and Disposition, 1986, 14(4), 509-11.

Pohl, L. R. et. al.; Determination of toxic pathways of metabolism by deuterium substitution; Drug Metabolism Reviews (1985), Volume Date 1984, 15(7), 1335-51.

Rampe, D. et. al.; Deuterated Analogs of verapamil and nifedipine. Synthesis and biological activity; Eur J Med Chem (1993) 28,259-263.

Helfenbein, J. et. al.; Isotopic Effect Study of Propofol Deuteration on the Metabolism, Activity, and Toxicity of the Anesthetic; J. Med. Chem. 2002, 45, 5806-5808.

Wen, L. et. al.; Simultaneous stereoselective analysis of venlafaxine and O-desmethylvenlafaxine enantiomers in human plasma by HPLC-ESI/MS using a vancomycin chiral column; Journal of Chromatography B, 2007, 850, 183-9 XP-22044059A.

Yardley, J.P. et. al.; 2-Phenyl-2-(1-hydroxycycloalkyl)ethylamine derivatives: synthesis and antidepressant activity; Journal of Medicinal Chemistry (1990), 33(10), 2899-905.

Nelson, SD et. al.; Primary and B-Secondary Deuterium Isotope Effects in N-Deethylation Reactions; Journal of Medicinal Chemistry, 1975, vol. 18, No. 11.

Farmer, PB et. al.; Synthesis, Metabolism, and Antitumor Activity of Deuterated Analogues of 1-(2-Choloroethyl)-3-cyclohexyl-1-nitrosourea; Journal of Medicinal Chemistry, 1978, vol. 21, No. 6, 514-20.

Borgstrom, L. et. al.; Comparative Pharmacokinetics of Unlabeled and Deuterium-Labeled Terbutaline: Demonstration of a Small Isotope Effect; Pharm Sci, 1988, 77(11), 952-4.

Browne, T.R.; Isotope effect: implications for pharmaceutical investigations; Pharmacochemistry Library (1997), 26 (Stable Isotopes in Pharmaceutical Research), 13-18.

Lessard, E. et. al.; Influence of CYP2D6 activity on the disposition and cardiovascular toxicity of the antidepressant agent venlafaxine in humans; Pharmacogenetics (1999), 9(4), 435-443.

Elison, C.; Effect of deuteration of N-CH$_{3}$ group on potency and enzymatic N-demethylation of morphine; Science, 1961, 134(3485), 1078-9.

Chavan, S.P. et. al.; An efficient and green protocol for the preparation of cycloalkanols: a practical synthesis of venlafaxine; Tetrahedron Letters (2004), 45(39), 7291-7295.

Morton, W.A. et. al.; Venlafaxine: a structurally unique and novel antidepressant; The Annals of pharmacotherapy (1995), 29(4), 387-95.

Reis, M. et. al.; Therapeutic drug monitoring of racemic venlafaxine and its main metabolites in an everyday clinical setting; Therapeutic Drug Monitoring (2002), 24(4), 545-553.

Foster, A.B.; Deuterium isotope effects in studies of drug metabolism; Trends in Pharmacological Sciences (1984), 5 (12), 524-7.

Gant, T. G. et. al.; Substituted Phenethylamines With Serotoninergic and/or Norepinephrinergic Activity; filed May 30, 2008; not yet published; U.S. Appl. No. 12/095,598.

Deschamps, F.; Synthese Aptochem Catalog Aug. 2007; XP-002490781.

Gant, Thomas, G., Sarshar, Sepehr, U.S. Appl. No. 11/565,451—Prosecution History, Substituted, Phenethylamines With Serotoninergic and/or Norepinephrinergic Activity, Auspex Pharmaceuticals, Inc.

Muth et al., Drug Development Research, 1991, 23, 191-199, Biochemical, Neurophysiological, and Behavioral Effects of WY-45,233 and Other Identified Metabolites of the Antidepressant Venlafaxine, 1991.

Baillie, Thomas, Pharmacological Reviews, 1981, 33(2), 81-132, The Use of Stable Isotopes in Pharmaceutical Research, 1981.

Browne, Thomas, J. Clin. Pharmacol., 1998, 38, 213-220, Stable Isotope Techniques in Early Drug Development: an Economic Evaluation, 1998.

Cherrah et al., Biomedical and Environmental Mass Spectrometry, 1987, 14, 653-657, Study of Deuterium Isotope Effects on Protein Binding by Gas Chromatography/Mass Spectrometry. Caffeine and Deuterated Isomers, 1987.

Dyck et al., J. Neurochem., 1986, 46(2), 399-404, Effects of Deuterium Substitution on the Catabolism of Beta-Phenethylamine: An In Vivo Study, 1986.

Gouyette, Alain, Biomedical and Environmental Mass Spectrometry, 1988, 15, 243-247, Use of Deuterium-Labelled Ellipntinium and its Use in Metabolic Studies, 1988.

Haskins, N.J., Biomedical Mass Spectrometry, 1982, 9(7), 269-277, The Application of Stable Isotopes in Biomedical Research, 1982.

Honma et al., Drug Metabolism and Disposition, 1987, 15(4), 551-559, The Metabolism of Roxatidine Acetate Hydrochloride, 1987.

Pieiaszek et al., J. Clin. Pharmacol., 1999, 39, 817-825, Moricizine Bioavailability Via Simultaneous, Dual, Stable Isotope Administration: Bioequivalence Implications, 1999.

Tonn et al., Biomedical Mass Spectrometry, 1993, 22, 633-642, Simultaneous Analysis of Diphenylhydramine and a Stable Isotope Analog (2H10)Diphenylhydramine Using Capillary Gas Chromatography With Mass Selective Detection in Biological Fluids From Chronically Instrumented Pregnant Ewes, 1993.

Wolen et al., J. Clin. Pharmacol., 1986, 26, 419-424, The Application of Stable Isotopes to Studies of Drug Bioavailibility and Bioequivalence, 1986.

Gant, Thomas, G., Sarshar, Sepehr, U.S. Appl. No. 12/048,012—Prosecution History, Substituted Phenethylamines With Serotoninergic and/or Norepinephrinergic Activity, Auspex Pharmaceuticals, Inc.

Gant, Thomas, G., Sarshar, Sepehr, U.S. Appl. No. 12/234,236—Prosecution History, Substituted Phenethylamines With Serotoninergic and/or Norepinephrinergic Activity, Auspex Pharmaceuticals, Inc.

Gant, Thomas, G., Sarshar, Sepehr, U.S. Appl. No. 12/095,598—Prosecution History, Substituted Phenethylamines With Serotoninergic and/or Norepinephrinergic Activity, Auspex Pharmaceuticals, Inc.

* cited by examiner

SUBSTITUTED PHENETHYLAMINES WITH SEROTONINERGIC AND/OR NOREPHRINERGIC ACTIVITY

CROSS-REFERENCE TO RELATED APPLICATIONS

This application is a division of application Ser. No. 11/565,451, entitled "SUBSTITUTED PHENETHYLAMINES WITH SEROTONINERGIC AND/OR NOREPINEPHRINERGIC ACTIVITY", filed Nov. 30, 2006 now U.S. Pat. No. 7,456,317, which claims priority to U.S. Provisional Application Nos. 60/741,315, entitled "SUBSTITUTED PHENETHYLAMINES WITH SEROTONINERGIC AND/OR NOREPINEPHRINERGIC ACTIVITY", filed Dec. 1, 2005; and 60/841,366, entitled "SUBSTITUTED PHENETHYLAMINES WITH SEROTONINERGIC AND/OR NOREPINEPHRINERGIC ACTIVITY, filed Aug. 30, 2006, all of which are incorporated by reference in their entireties.

BACKGROUND OF THE INVENTION

1. Field of the Invention

The present invention is directed to inhibitors of the uptake of monoamine neurotransmitters and pharmaceutically acceptable salts and prodrugs thereof, the chemical synthesis thereof, and the medical use of such compounds for the treatment and/or management of psychotropic disorders, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, and/or premature ejaculation.

2. Description of the Related Art

In an attempt to breakdown or to help solubilize chemicals and nutrients that have been absorbed into the blood, the human body expresses various enzymes (e.g. the cytochrome $P_{450}$ enzymes or CYPs, esterases, proteases, reductases, dehydrogenases, and the like) that react with the chemicals and nutrients to produce novel intermediates or metabolites. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions, and can have substantially different pharmacokinetic, pharmacodynamic, acute and long-term toxicity profiles relative to the parent compounds. For most drugs, such oxidations are generally rapid and ultimately lead to administration of multiple or high daily doses. There is therefore an obvious and immediate need for improvements of such drugs.

Chemical kinetics is the study of reaction rates. The activation energy $E_{act}$ in chemistry is the energy that must be supplied to a system in order to initiate a particular chemical process. In other words, this is the minimum energy required for a specific chemical reaction to take place. A reaction will occur between two properly oriented molecules if they possess a minimum requisite energy. During the approach, the outer shell electrons of each molecule will induce repulsion. Overcoming this repulsion requires an input of energy (i.e. the activation energy), which results from the heat of the system; i.e. the translational, vibrational, and rotational energy of each molecule. If sufficient energy is available, the molecules may attain the proximity and orientation necessary to cause a rearrangement of bonds to form new substances.

The relationship between the activation energy and the rate of reaction may be quantified by the Arrhenius equation which states that the fraction of molecules that have enough energy to overcome an energy barrier—those with energy at least equal to the activation energy, $E_{act}$—depends exponentially on the ratio of the activation to thermal energy $k=Ae^{-Eact/RT}$. In this equation, RT is the average amount of thermal energy that molecules possess at a certain temperature T, where R is the molar gas constant, k is the rate constant for the reaction and A (the frequency factor) is a constant specific to each reaction that depends on the probability that the molecules will collide with the correct orientation.

The transition state in a reaction is a short lived state (on the order of $10^{-14}$ sec) along the reaction pathway during which the original bonds have stretched to their limit. By definition, the activation energy $E_{act}$ for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or the new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) is two-fold more massive than hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the Deuterium Kinetic Isotope Effect (DKIE) and can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom, and occurs because transition states involving a proton can sometimes form in the absence of the required activation energy. A deuterium is larger and statistically has a much lower probability of undergoing this phenomenon. Substitution of tritium for hydrogen results in yet a stronger bond than deuterium and gives numerically larger isotope effects.

Discovered in 1932 by Urey, deuterium (D) is a stable and non-radioactive isotope of hydrogen. It was the first isotope to be separated from its element in pure form and is twice as massive as hydrogen, and makes up about 0.02% of the total mass of hydrogen (in this usage meaning all hydrogen isotopes) on earth. When two deuteriums bond with one oxygen, deuterium oxide ($D_2O$ or "heavy water") is formed. $D_2O$ looks and tastes like $H_2O$ but it has different physical properties. It boils at 101.41° C. and freezes at 3.79° C. Its heat capacity, heat of fusion, heat of vaporization, and entropy are all higher than $H_2O$. It is also more viscous and is not as powerful a solvent as $H_2O$.

Tritium (T) is a radioactive isotope of hydrogen, used in research, fusion reactors, neutron generators and radiopharmaceuticals. Mixing tritium with a phosphor provides a continuous light source, a technique that is commonly used in wristwatches, compasses, rifle sights and exit signs. It was discovered by Rutherford, Oliphant and Harteck in 1934 and is produced naturally in the upper atmosphere when cosmic rays react with $H_2$ molecules. Tritium is a hydrogen atom that has 2 neutrons in the nucleus and has an atomic weight close to 3. It occurs naturally in the environment in very low concentrations, most commonly found as $T_2O$, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk.

When pure $D_2O$ is given to rodents, it is readily absorbed and reaches an equilibrium level that is usually about eighty percent of the concentration that is consumed by the animals. The quantity of deuterium required to induce toxicity is extremely high. When 0 to as much as 15% of the body water has been replaced by $D_2O$, animals are healthy but are unable to gain weight as fast as the control (untreated) group. Between 15 to 20% $D_2O$, the animals become excitable. At 20 to 25%, the animals are so excitable that they go into frequent convulsions when stimulated. Skin lesions, ulcers on the paws and muzzles, and necrosis of the tails appear. The animals also become very aggressive; males becoming almost unmanageable. At 30%, the animals refuse to eat and become comatose. Their body weight drops sharply and their metabolic rates drop far below normal, with death occurring at 30 to 35% replacement. The effects are reversible unless more than thirty percent of the previous body weight has been lost due to $D_2O$, Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles, has been demonstrated previously with some classes of drugs. For example, DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching which may even give rise to an oxidative intermediate with a faster off-rate from an activating Phase I enzyme (e.g. cytochrome $P_{450}$ 3A4). The concept of metabolic switching asserts that xenogens, when sequestered by Phase I enzymes, may bind transiently and re-bind in a variety of conformations prior to the chemical reaction (e.g. oxidation). This claim is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such pitfalls are non-obvious and have not been heretofore sufficiently predictable a priori for any drug class.

It has been hypothesized that the efficacy of venlafaxine (Effexor®) is mainly due to its ability to inhibit serotonin reuptake and, potentially, norepinephrine reuptake in neuronal cells. The latter is purported to take effect only at high doses. The drug substance is sold as a 50/50 racemic mixture of R- and S-enantiomers. The mechanism of action of this drug has been extensively studied.

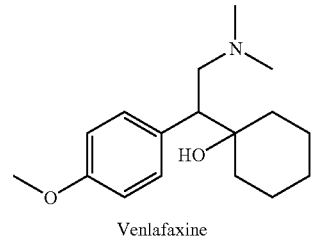

Venlafaxine

The benefits and shortcomings of this drug have been extensively reviewed as well. Some of these shortcomings can be traced to metabolism-related phenomena. Venlafaxine is converted in vivo by oxidative and conjugative degradation to multiple metabolites, at least 48 of which are documented. The major metabolites include much phase I metabolism leading to demethylation at the oxygen and/or nitrogen centers, and cyclohexyl ring hydroxylation, as well as significant phase II metabolism including glucuronidation of the hydroxylated metabolites. Because this drug is metabolized by polymorphically-expressed isozymes of cytochrome $P_{450}$ including CYPs 2C19 and 2D6, and because it can act as an inhibitor of CYP2D6, its application in polypharmacy is necessarily complex and has potential for adverse events. These CYPs are involved in the metabolism of many medications that are typically prescribed concurrently with venlafaxine. This phenomenon increases inter-patient variability in response to polypharmacy. An example of the critical need for improvement is the published interpatient variability observed in "poor metabolizers" having either defective CYP2D6 alleles or total lack of CYP2D6 expression. These patients fail to convert venlafaxine to its equipotent metabolite, O-desmethylvenlafaxine. Venlafaxine also suffers from a short half-life relative to the majority of serotonin reuptake inhibitors. The half-life of venlafaxine in humans is ~5 hours, while its active metabolite has a $T_{1/2}$ of ~11 hours. As a consequence of its 5-11 hour pharmacological half-life, those taking venlafaxine are at significant risk of SRI discontinuation symptoms if the drug is abruptly discontinued. Furthermore, in order to overcome its short half-life, the drug must be taken 2 (BID) or 3 (TID) times a day, which increases the probability of patient incompliance and discontinuance. Most other serotonin reuptake inhibitors (SRIs) have half-lives≧24 hours. A 24-72 hour half-life is regarded as ideal for this class of compounds by most clinicians. There is therefore an obvious and immediate need for improvements in the development of monoamine reuptake inhibitors such as paroxetine.

SUMMARY OF THE INVENTION

Disclosed herein are compounds of Formula 1:

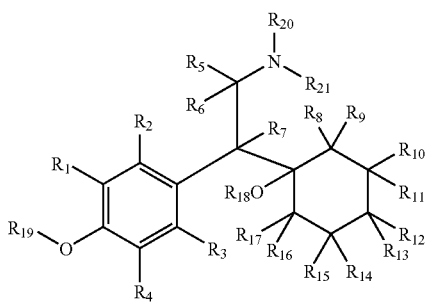

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof, wherein:

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from the group consisting of hydrogen, and deuterium;

$R_{19}$, $R_{20}$, and $R_{21}$ are independently selected from the group consisting of —$CH_3$, —$CH_2D$, —$CHD_2$, and —$CD_3$;

provided that compounds of Formula 1 contain at least one deuterium atom; and provided that deuterium enrichment in compounds of Formula 1 is at least about 1%.

Also disclosed herein are pharmaceutical compositions comprising a compound of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, with a pharmaceutically acceptable carrier.

Further, disclosed herein are methods of eliciting, modulating and/or regulating the reuptake of monoamine neurotransmitters including serotonin and/or norepinephrine.

In addition, disclosed herein are methods of treating a mammalian subject having, suspected of having, or being prone to a disease or condition, such as a disease or condition selected from the group consisting of anxiety disorder, generalized anxiety disorder, depression, post-traumatic stress disorder, obsessive-compulsive disorder, panic disorder, a hot flash, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, and/or premature ejaculation.

DETAILED DESCRIPTION OF THE INVENTION

Certain monoamine reuptake inhibitors are known in the art and are shown herein. Venlafaxine (Effexor®) is one such compound. The carbon-hydrogen bonds of venlafaxine contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation produce a detectable Kinetic Isotope Effect (KIE) that could affect the pharmacokinetic, pharmacologic and/or toxicologic parameters of such monoamine reuptake inhibitors relative to compounds having naturally occurring levels of deuterium. Aspects of the present invention disclosed herein describe a novel approach to designing and synthesizing new analogs of these monoamine reuptake inhibitors through chemical modifications and derivations of the carbon-hydrogen bonds of the modulators and/or of the chemical precursors used to synthesize said modulators. Suitable modifications of certain carbon-hydrogen bonds into carbon-deuterium bonds may generate novel monoamine reuptake inhibitors with unexpected and non-obvious improvements of pharmacological, pharmacokinetic and toxicological properties in comparison to the non-isotopically enriched monoamine reuptake inhibitors. This invention relies on the judicious and successful application of chemical kinetics to drug design. Deuterium incorporation levels in the compounds of the invention are significantly higher than the naturally-occurring levels and are sufficient to induce at least one substantial improvement as described herein.

Information has come to light that enables the judicious use of deuterium in solving the PD and Absorption, Distribution, Metabolism, Excretion, and Toxicological (ADMET) shortcomings for venlafaxine. For example, both N-methyl groups, the single O-methyl, and several sites on the cyclohexyl ring of venlafaxine are now known to be sites of cytochrome $P_{450}$ metabolism. The toxicities of all resultant metabolites are not known. Furthermore, because polymorphically expressed CYPs such as 2C19 and 2D6 oxidize venlafaxine, and because venlafaxine inhibits the polymorphically expressed CYP2D6, the prevention of such interactions decreases interpatient variability, decreases drug-drug interactions, increases $T_{1/2}$, decreases the necessary $C_{max}$, and improves several other ADMET parameters. For example, the half-life of the parent drug of venlafaxine ranges from 3-7 hours. The equipotent metabolite, O-demethylated venlafaxine, has a half-life averaging 11 hours. Various deuteration patterns can be used to a) alter the ratio of active metabolites, b) reduce or eliminate unwanted metabolites, c) increase the half-life of the parent drug, and/or d) increase the half-life of active metabolites and create a more effective drug and a safer drug for polypharmacy, whether the polypharmacy be intentional or not. High doses of venlafaxine are often prescribed in order to reach levels capable of inhibiting norepinephrine reuptake. Unfortunately, high doses are also associated with hypertension. Since these phenomenon are linked by the pharmaceutical agent rather than the pharmacological target, the two phenomena are theoretically separable by increasing the half-life thus allowing dosing in a range that lowers the $C_{max}$ and thus may avoid triggering the mechanism leading to hypertension. Further illustrating this point, venlafaxine is known to display linear kinetics at the low end of the dose range, 75 mg/day, but displays non-linear kinetics at the high end of the dose range, ~400 mg/day, as a result of the saturation of clearance mechanisms. This non-linearity produces an ascending, rather than a flat, dose-response curve for venlafaxine. The deuteration approach has strong potential to slow metabolism through the previously saturated mechanism allowing linear, more predictable ADMET responses throughout the dose range (which would also be lower via this invention). This leads to lesser interpatient variability of the type that can lead to the hypertensive effects.

The deuterated analogs of this invention have the potential to uniquely maintain the beneficial aspects of the non-isotopically enriched drugs while substantially increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions. These drugs also have strong potential to reduce the cost-of-goods (COG) owing to the ready availability of inexpensive sources of deuterated reagents combined with previously mentioned potential for lowering the therapeutic dose. The present inventors have discovered that deuteration at the methylenedioxy moiety alone, and/or deuteration at the methylenedioxy moiety plus deuteration of additional sites found to be labile as a result of metabolic switching are effective in achieving some of the objectives disclosed herein.

Thus, in one aspect, there are provided herein compounds having the structural Formula 1:

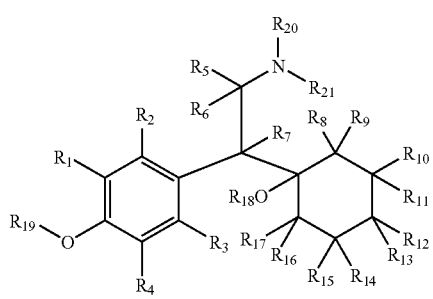

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof, wherein:

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from the group consisting of hydrogen, and deuterium;

$R_{19}$, $R_{20}$, and $R_{21}$ are independently selected from the group consisting of —$CH_3$, —$CH_2D$, —$CHD_2$, and —$CD_3$;

provided that compounds of Formula 1 contain at least one deuterium atom; and provided that deuterium enrichment in compounds of Formula 1 is at least about 1%.

Compounds of this invention have the potential to uniquely maintain the beneficial aspects of non-isotopically enriched monoamine reuptake inhibitors while substantially altering the half-life ($T_{1/2}$), lowering the maximum plasma concentration ($C_{max}$) of the minimum efficacious dose (MED), lowering the efficacious dose and thus decreasing non-mechanism-related toxicities and/or lowering the probability of drug-drug interactions. These drugs also have potential to reduce the cost-of-goods (COG) due to a potential for lowering the therapeutic dose when compared to the non-isotopically enriched monoamine reuptake inhibitors. In sum, many aspects of ADMET of the non-isotopically enriched monoamine reuptake inhibitors are substantially improved by this invention.

In some embodiments, agents in the present invention will expose patients to a maximum of about 0.000005% $D_2O$ (can also be expressed as about 0.00001% DHO). This quantity is a small fraction of the naturally occurring background levels of $D_2O$ (or DHO) in circulation. This maximum exposure limit is obtained if all of the C-D bonds of the deuterium-enriched drug are metabolized. However, because of the DKIE, most if not all, of the C-D bonds of the deuterium-enriched drug will not be metabolized prior to excretion of said deuterium-enriched drug from the subject. Therefore, the actual exposure of the patient to $D_2O$ will be far less than the aforementioned maximum limit. As discussed above, the levels of $D_2O$ shown to cause toxicity in animals is much greater than even the maximum limit of exposure because of the deuterium enriched drug. The deuterium-enriched compounds of the present invention, therefore, do not cause any additional toxicity because of the use of deuterium.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%. In some embodiments, the deuterium enrichment in the compounds of the present invention is greater than 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

"Isotopic enrichment" refers to the percentage of incorporation of a less prevalent isotope of an element at a given site on the molecule instead of the more prevalent isotope of the element. "Non-isotopically enriched" refers to a molecule in which the percentage of the various isotopes is substantially the same as the naturally occurring percentages.

In certain embodiments, the compound of Formula 1 contains about 60% or more by weight of the (−)-enantiomer of the compound and about 40% or less by weight of (+)-enantiomer of the compound. In some embodiments, the compound of Formula 1 contains about 70% or more by weight of the (−)-enantiomer of the compound and about 30% or less by weight of (+)-enantiomer of the compound. In some embodiments, the compound of Formula 1 contains about 80% or more by weight of the (−)-enantiomer of the compound and about 20% or less by weight of (+)-enantiomer of the compound. In some embodiments, the compound of Formula 1 contains about 90% or more by weight of the (−)-enantiomer of the compound and about 10% or less by weight of the (+)-enantiomer of the compound. In some embodiments, the compound of Formula 1 contains about 95% or more by weight of the (−)-enantiomer of the compound and about 5% or less by weight of (+)-enantiomer of the compound. In some embodiments, the compound of Formula 1 contains about 99% or more by weight of the (−)-enantiomer of the compound and about 1% or less by weight of (+)-enantiomer of the compound.

In certain other embodiments, the compound of Formula 1 contains about 60% or more by weight of the (+)-enantiomer of the compound and about 40% or less by weight of (−)-enantiomer of the compound. In some embodiments, the compound of Formula 1 contains about 70% or more by weight of the (+)-enantiomer of the compound and about 30% or less by weight of (−)-enantiomer of the compound. In some embodiments, the compound of Formula 1 contains about 80% or more by weight of the (+)-enantiomer of the compound and about 20% or less by weight of (−)-enantiomer of the compound. In some embodiments, the compound of Formula 1 contains about 90% or more by weight of the (+)-enantiomer of the compound and about 10% or less by weight of the (−)-enantiomer of the compound. In some embodiments, the compound of Formula 1 contains about 95% or more by weight of the (+)-enantiomer of the compound and about 5% or less by weight of (−)-enantiomer of the compound. In some embodiments, the compound of Formula 1 contains about 99% or more by weight of the (+)-enantiomer of the compound and about 1% or less by weight of (−)-enantiomer of the compound.

In certain embodiments, $R_1$ is hydrogen. In other embodiments, $R_2$ is hydrogen. In some embodiments, $R_3$ is hydrogen. In other embodiments, $R_4$ is hydrogen. In yet other embodiments, $R_5$ is hydrogen. In still other embodiments, $R_6$ is hydrogen. In yet other embodiments, $R_7$ is hydrogen. In yet other embodiments, $R_8$ is hydrogen. In still other embodiments, $R_9$ is hydrogen. In still other embodiments, $R_{10}$ is hydrogen. In other embodiments, $R_{11}$ is hydrogen. In some embodiments, $R_{12}$ is hydrogen. In other embodiments, $R_{13}$ is hydrogen. In still other embodiments, $R_{14}$ is hydrogen. In yet other embodiments, $R_{15}$ is hydrogen. In yet other embodiments, $R_{16}$ is hydrogen. In still other embodiments, $R_{17}$ is hydrogen. In yet other embodiments, $R_{18}$ is hydrogen.

In certain embodiments, $R_1$ is deuterium. In other embodiments, $R_2$ is deuterium. In some embodiments, $R_3$ is deuterium. In other embodiments, $R_4$ is deuterium. In yet other embodiments, $R_5$ is deuterium. In still other embodiments, $R_6$ is deuterium. In yet other embodiments, $R_7$ is deuterium. In yet other embodiments, $R_8$ is deuterium. In still other embodiments, $R_9$ is deuterium. In still other embodiments, $R_{10}$ is deuterium. In other embodiments, $R_{11}$ is deuterium. In some embodiments, $R_{12}$ is deuterium. In other embodiments, $R_{13}$ is deuterium. In still other embodiments, $R_{14}$ is deuterium. In yet other embodiments, $R_{15}$ is deuterium. In yet other embodiments, $R_{16}$ is deuterium. In still other embodiments, $R_{17}$ is deuterium. In yet other embodiments, $R_{18}$ is deuterium.

In certain embodiments, $R_1$ is not hydrogen. In other embodiments, $R_2$ is not hydrogen. In some embodiments, $R_3$ is not hydrogen. In other embodiments, $R_4$ is not hydrogen. In yet other embodiments, $R_5$ is not hydrogen. In still other embodiments, $R_6$ is not hydrogen. In yet other embodiments, $R_7$ is not hydrogen. In yet other embodiments, $R_8$ is not hydrogen. In still other embodiments, $R_9$ is not hydrogen. In still other embodiments, $R_{10}$ is not hydrogen. In other embodiments, $R_{11}$ is not hydrogen. In some embodiments, $R_{12}$ is not hydrogen. In other embodiments, $R_{13}$ is not hydrogen. In still other embodiments, $R_{14}$ is not hydrogen. In yet other embodiments, $R_{15}$ is not hydrogen. In yet other embodiments, $R_{16}$ is not hydrogen. In yet other embodiments, $R_{17}$ is not hydrogen. In still other embodiments, $R_{18}$ is not hydrogen.

In certain embodiments, $R_1$ is not deuterium. In other embodiments, $R_2$ is not deuterium. In some embodiments, $R_3$ is not deuterium. In other embodiments, $R_4$ is not deuterium. In yet other embodiments, $R_5$ is not deuterium. In still other embodiments, $R_6$ is not deuterium. In yet other embodiments, $R_7$ is not deuterium. In yet other embodiments, $R_8$ is not deuterium. In still other embodiments, $R_9$ is not deuterium. In still other embodiments, $R_{10}$ is not deuterium. In other embodiments, $R_{11}$ is not deuterium. In other embodiments, $R_{12}$ is not deuterium. In other embodiments, $R_{13}$ is not deuterium. In still other embodiments, $R_{14}$ is not deuterium. In yet other embodiments, $R_{15}$ is not deuterium. In yet other embodiments, $R_{16}$ is not deuterium. In yet other embodiments, $R_{17}$ is not deuterium. In still other embodiments, $R_{18}$ is not hydrogen.

In further embodiments, $R_{19}$ is —$CH_3$. In other embodiments, $R_{20}$ is —$CH_3$. In still other embodiments, $R_{21}$ is —$CH_3$.

In further embodiments, $R_{19}$ is —$CD_3$. In other embodiments, $R_{20}$ is —$CD_3$. In still other embodiments, $R_2$, is —$CD_3$.

In further embodiments, $R_{19}$ is not —$CH_3$. In other embodiments, $R_{20}$ is not —$CH_3$. In still other embodiments, $R_{21}$ is not —$CH_3$.

In further embodiments, $R_{19}$ is not —$CD_3$. In other embodiments, $R_{20}$ is not —$CD_3$. In still other embodiments, $R_{21}$ is not —$CD_3$.

In another embodiment of the invention, there are provided pharmaceutical compositions comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, for enteral, intravenous infusion, oral, parenteral, topical and/or ocular administration.

In yet another embodiment of the invention, there are provided pharmaceutical compositions comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, in a pharmaceutically acceptable vehicle, carrier, diluent, or excipient, or a combination thereof, for the treatment of conditions involving the inhibition of monoamine reuptake.

In another embodiment of the invention, there are provided methods of modulating monoamine reuptake, with one or more of the compounds or compositions of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof.

In yet another embodiment of the invention, there are provided compounds according to Formula 1 having one of the following structures:

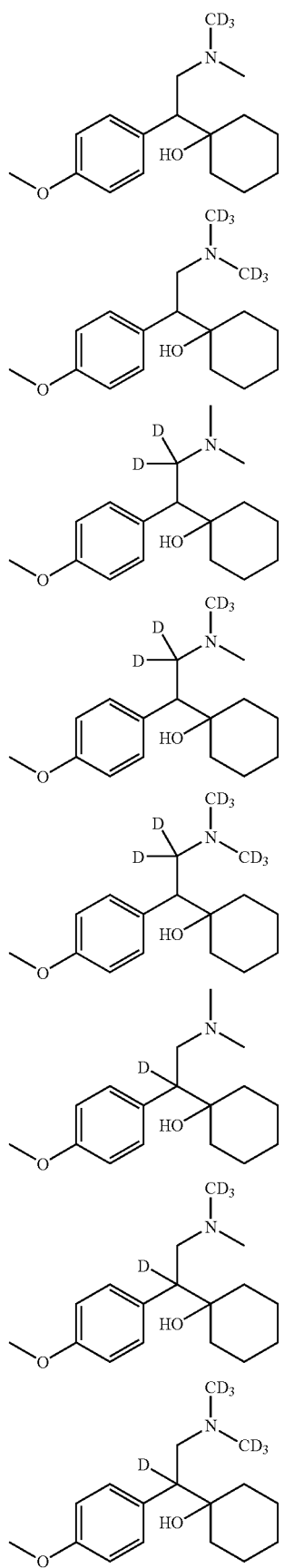
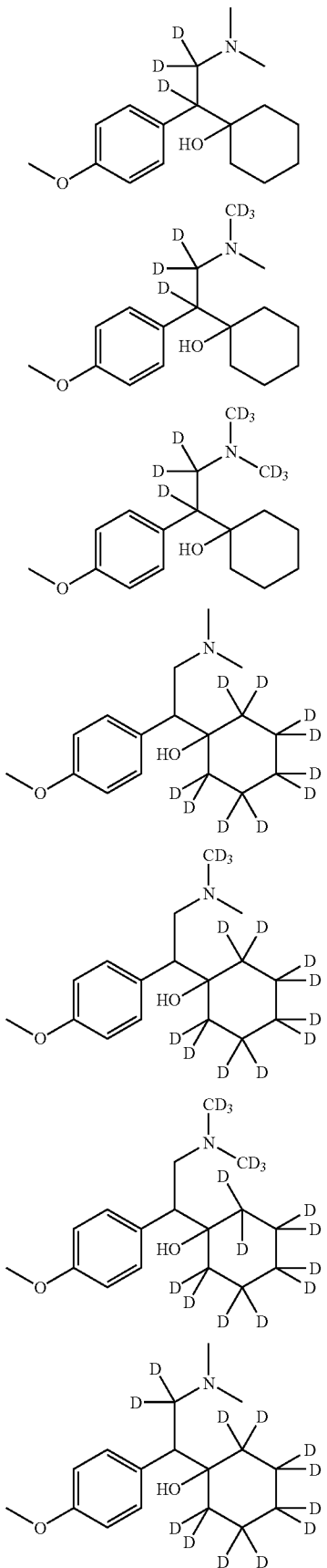

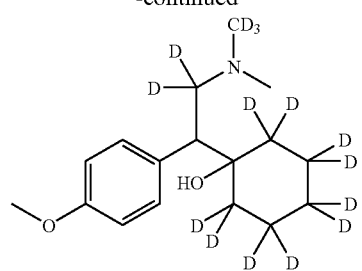
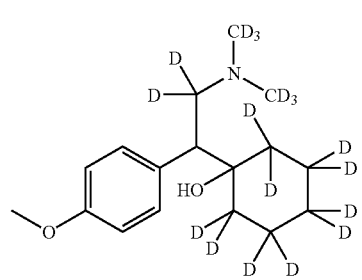
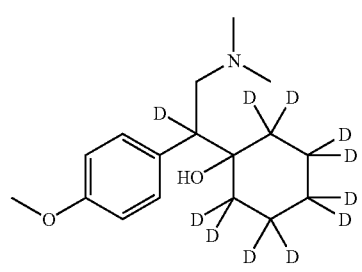
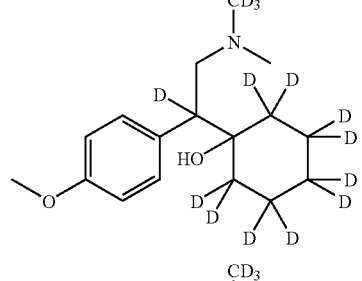
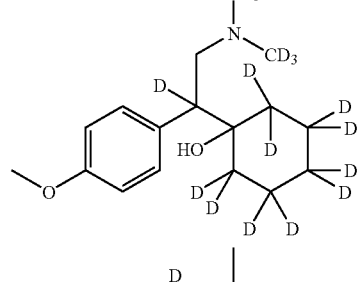
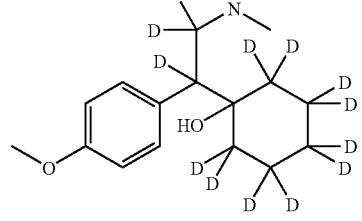
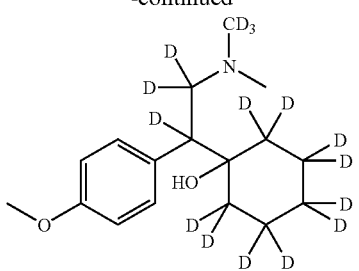
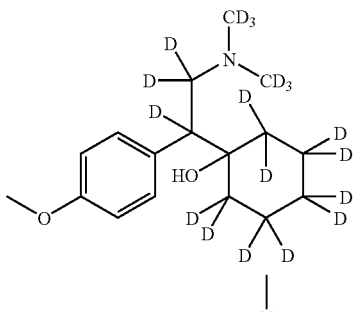
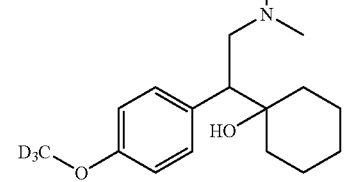
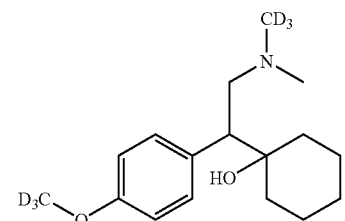
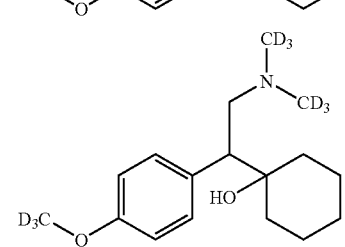
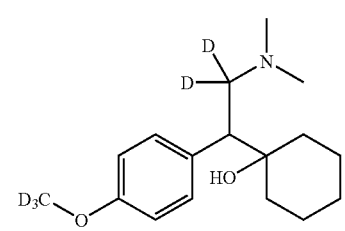
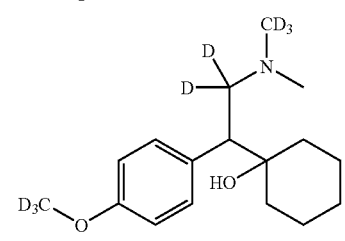

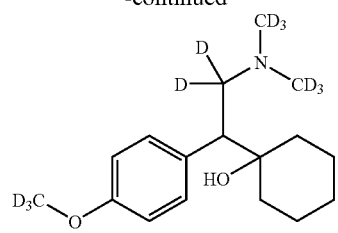
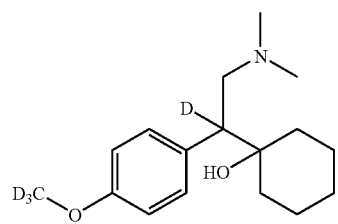
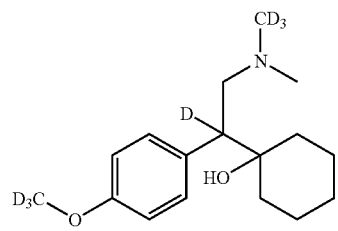
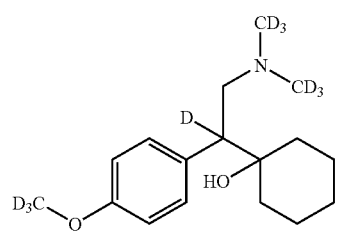
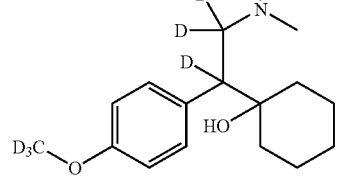
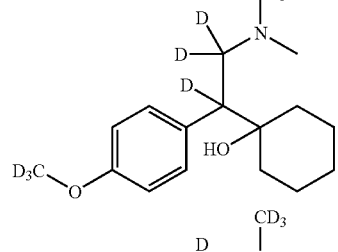
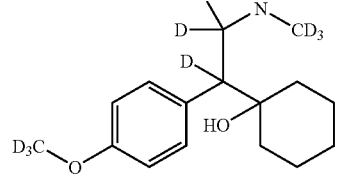
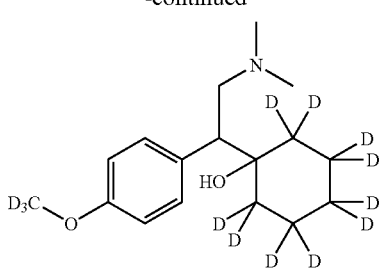
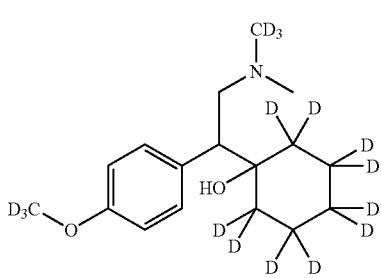
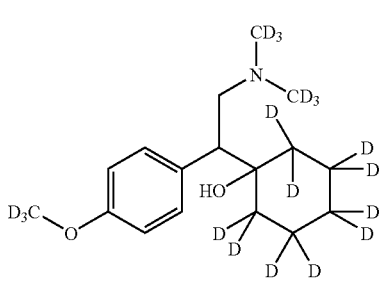
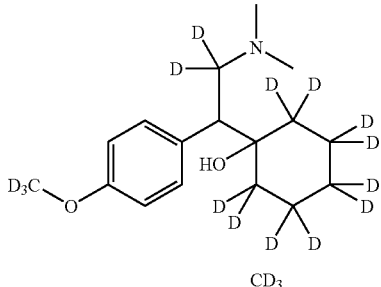
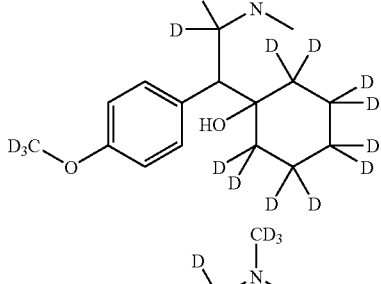
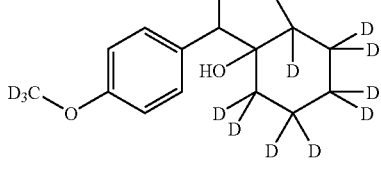

17
-continued
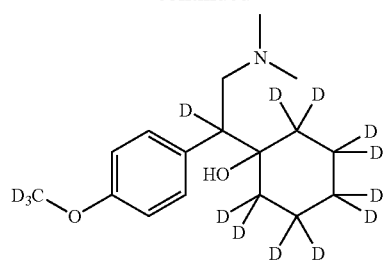
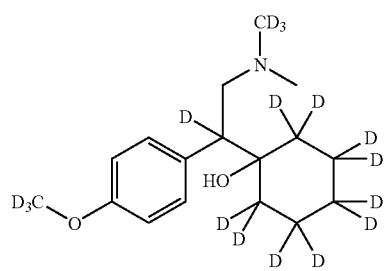
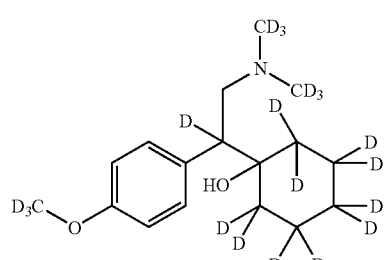
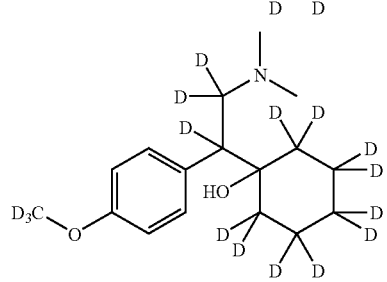
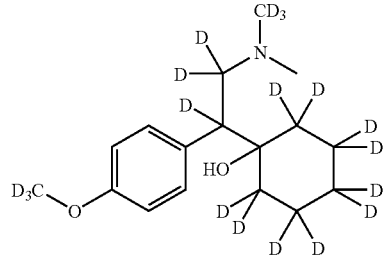
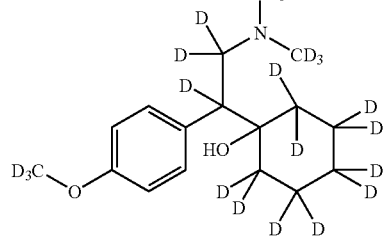
18
-continued
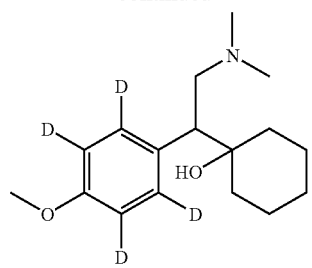
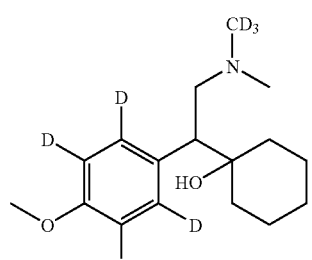
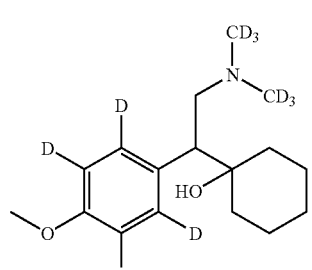
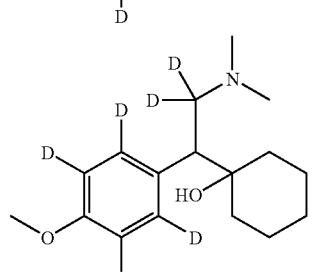
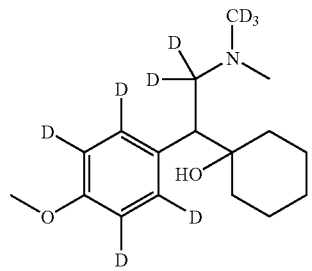
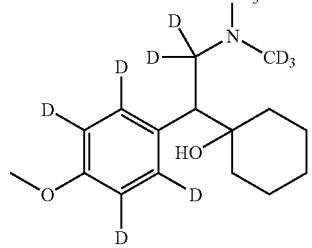

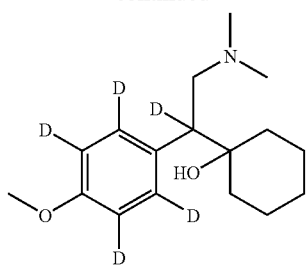
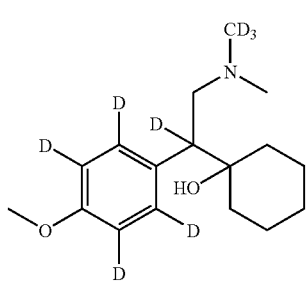
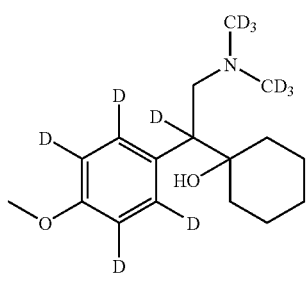
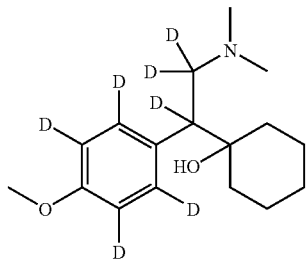
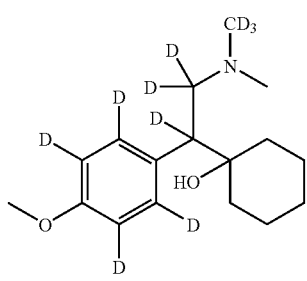
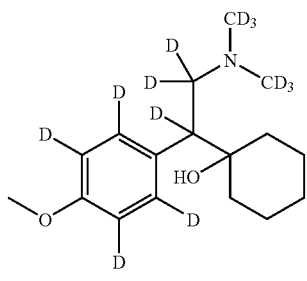
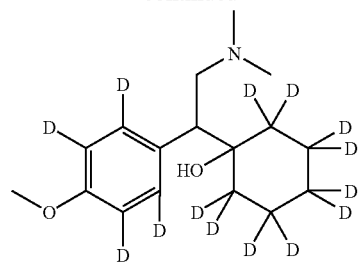
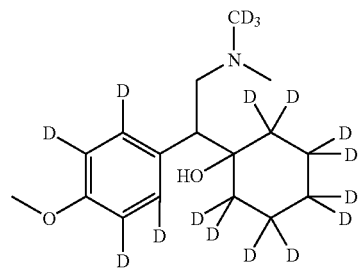
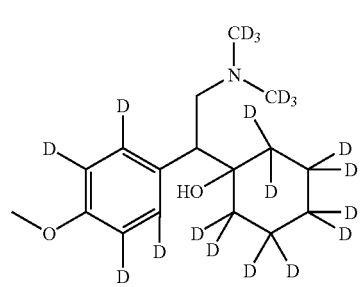
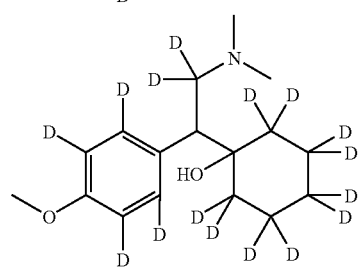
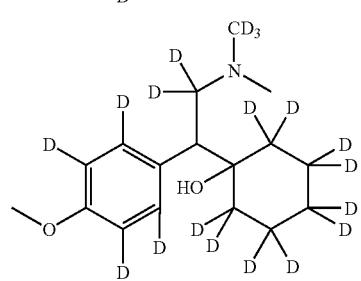
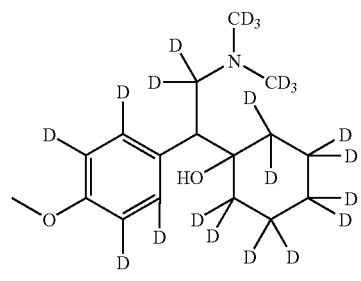

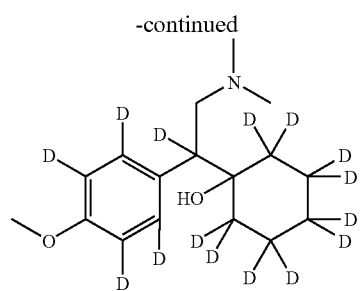
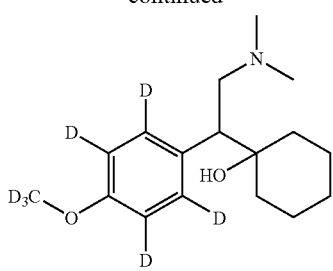
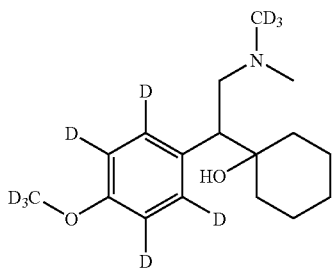
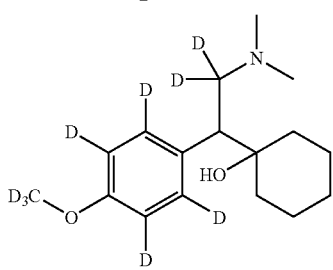
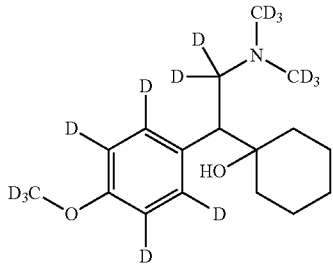

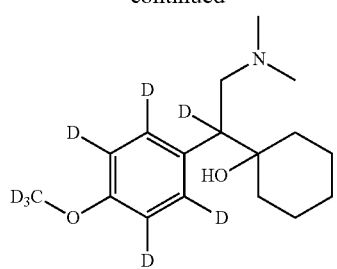
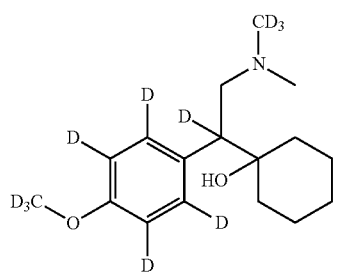
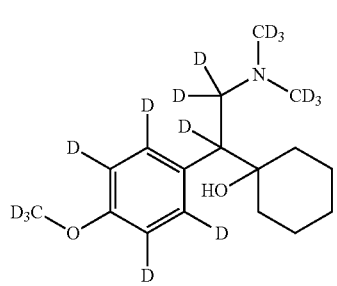
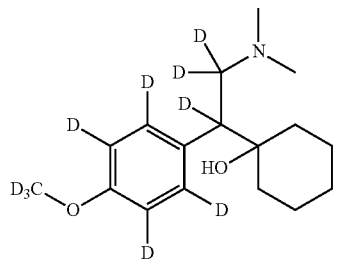
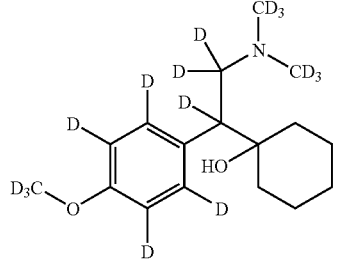
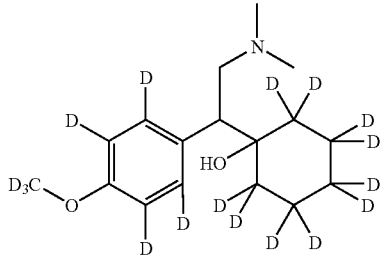
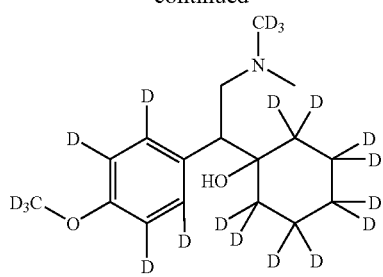
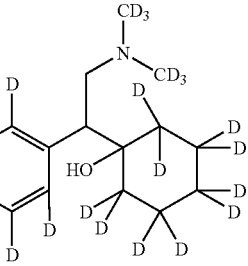
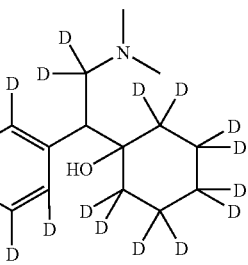
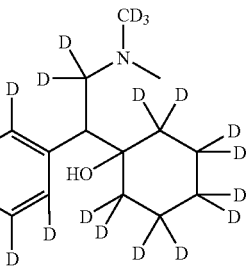
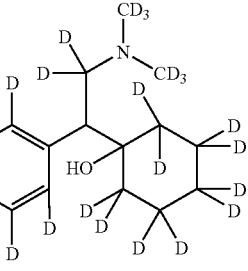
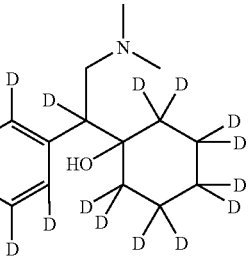

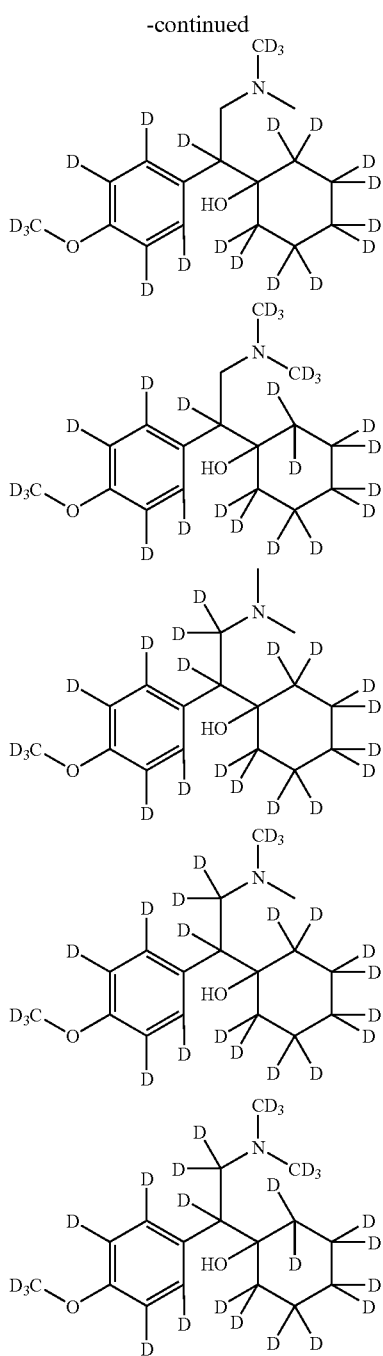

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, a mixture of diastereomers, or a pharmaceutically acceptable salt, solvate, or prodrug thereof.

The present invention is intended to include all isotopes of all atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopes of sulfur include $^{32}S$, $^{33}S$, $^{34}S$, and $^{36}S$. Isotopes of nitrogen include $^{14}N$ and $^{15}N$. Isotopes of oxygen include $^{16}O$, $^{17}O$, and $^{18}O$.

Isotopic hydrogen can be introduced into organic molecules by synthetic techniques that employ deuterated reagents whereby incorporation rates are pre-determined and/or by exchange techniques wherein incorporation rates are determined by equilibrium conditions and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. In addition, the molecule being labeled may be changed, depending upon the severity of the synthetic reaction employed. Exchange techniques, on the other hand, may yield lower tritium or deuterium incorporation, often with the isotope being distributed over many sites on the molecule, but offer the advantage that they do not require separate synthetic steps and are less likely to disrupt the structure of the molecule being labeled.

In another aspect of the invention, there are provided methods of treating a mammalian subject, particularly a human, suspected of having, or being prone to a disease or condition involving monoamine reuptake, comprising administering to a mammalian subject in need thereof a therapeutically effective amount of a compound of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof.

In some embodiments, the administering step in the above methods comprises administering the compound of the invention in some composition, such as for example a single tablet, pill, capsule, a single solution for intravenous injection, a single drinkable solution, a single dragee formulation or patch, and the like wherein the amount administered is about 0.5 milligram to 400 milligram total daily dose.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect decreased inter-individual variation in plasma levels of said compound or a metabolite thereof during treatment of the above-mentioned diseases as compared to the non-isotopically enriched compound.

In some embodiments, the inter-individual variation in plasma levels of the compounds of the invention, or metabolites thereof, is decreased by greater than about 5%, as compared to the non-isotopically enriched compounds. In other embodiments, the inter-individual variation in plasma levels of the compounds of the invention, or metabolites thereof, is decreased by greater than about 10%, as compared to the non-isotopically enriched compounds. In other embodiments, the inter-individual variation in plasma levels of the compounds of the invention, or metabolites thereof, is decreased by greater than about 20%, as compared to the non-isotopically enriched compounds. In other embodiments, the inter-individual variation in plasma levels of the compounds of the invention, or metabolites thereof, is decreased by greater than about 30%, as compared to the non-isotopically enriched compounds. In other embodiments, the inter-individual variation in plasma levels of the compounds of the invention, or metabolites thereof, is decreased by greater than about 40%, as compared to the non-isotopically enriched compounds. In other embodiments, the inter-individual variation in plasma levels of the compounds of the invention, or metabolites thereof, is decreased by greater than about 50%, as compared to the non-isotopically enriched compounds. Plasma levels of the compounds of the invention, or metabolites thereof, are measured by the methods of Li et al *Rapid Communications in Mass Spectrometry* 2005, 19(14), 1943-1950, which is hereby incorporated by reference in its entirety.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect increased average plasma levels of said compound or decreased average plasma levels of at least one metabolite of said compound per dosage unit as compared to the non-isotopically enriched compound.

In some embodiments, the average plasma levels of the compounds of the invention are increased by greater than about 5%, as compared to the non-isotopically enriched compounds. In other embodiments, the average plasma levels of the compounds of the invention are increased by greater than about 10%, as compared to the non-isotopically enriched compounds. In other embodiments, the average plasma levels of the compounds of the invention are increased by greater than about 20%, as compared to the non-isotopically enriched compounds. In other embodiments, the average plasma levels of the compounds of the invention are increased by greater than about 30%, as compared to the non-isotopically enriched compounds. In other embodiments, the average plasma levels of the compounds of the invention are increased by greater than about 40%, as compared to the non-isotopically enriched compounds. In other embodiments, the average plasma levels of the compounds of the invention are increased by greater than about 50%, as compared to the non-isotopically enriched compounds.

In some embodiments, the average plasma levels of a metabolite of the compounds of the invention are decreased by greater than about 5%, as compared to the non-isotopically enriched compounds. In other embodiments, the average plasma levels of a metabolite of the compounds of the invention are decreased by greater than about 10%, as compared to the non-isotopically enriched compounds. In other embodiments, the average plasma levels of a metabolite of the compounds of the invention are decreased by greater than about 20%, as compared to the non-isotopically enriched compounds. In other embodiments, the average plasma levels of a metabolite of the compounds of the invention are decreased by greater than about 30%, as compared to the non-isotopically enriched compounds. In other embodiments, the average plasma levels of a metabolite of the compounds of the invention are decreased by greater than about 40%, as compared to the non-isotopically enriched compounds. In other embodiments, the average plasma levels of a metabolite of the compounds of the invention are decreased by greater than about 50%, as compared to the non-isotopically enriched compounds.

Plasma levels of the compounds of the invention, or metabolites thereof, are measured by the methods of Li et al *Rapid Communications in Mass Spectrometry* 2005, 19(14), 1943-1950, which is hereby incorporated by reference in its entirety.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising a least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect a decreased inhibition of, and/or metabolism by at least one cytochrome $P_{450}$ isoform in mammalian subjects during treatment of the above-mentioned diseases as compared to the non-isotopically enriched compound. Examples of cytochrome $P_{450}$ isoforms in mammalian subjects include CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4x1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51 and the like.

In some embodiments, the decrease in inhibition of the cytochrome $P_{450}$ isoform by compounds of the invention is greater than about 5%, as compared to the non-isotopically enriched compounds. In other embodiments, the decrease in inhibition of the cytochrome $P_{450}$ isoform by compounds of the invention is greater than about 10%, as compared to the non-isotopically enriched compounds. In other embodiments, the decrease in inhibition of the cytochrome $P_{450}$ isoform by compounds of the invention is greater than about 20%, as compared to the non-isotopically enriched compounds. In other embodiments, the decrease in inhibition of the cytochrome $P_{450}$ isoform by compounds of the invention is greater than about 30%, as compared to the non-isotopically enriched compounds. In other embodiments, the decrease in inhibition of the cytochrome $P_{450}$ isoform by compounds of the invention is greater than about 40%, as compared to the non-isotopically enriched compounds. In other embodiments, the decrease in inhibition of the cytochrome $P_{450}$ isoform by compounds of the invention is greater than about 50%, as compared to the non-isotopically enriched compounds.

The inhibition of the cytochrome $P_{450}$ isoform is measured by the methods of Ko et al *British Journal of Clinical Pharmacology* 2000, 49(4), 343-351, which is hereby incorporated by reference its entirety.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising a least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect a decreased metabolism via at least one polymorphically-expressed cytochrome $P_{450}$ isoform in mammalian subjects during treatment of the above-mentioned diseases as compared to the non-isotopically enriched compound. Examples of polymorphically-expressed cytochrome $P_{450}$ isoforms in mammalian subjects include CYP2C8, CYP2C9, CYP2C19, and CYP2D6.

In some embodiments, the decrease in metabolism of compounds of the invention by the cytochrome P450 isoform is greater than about 5%, as compared to the non-isotopically enriched compound. In other embodiments, the decrease in metabolism of compounds of the invention by the cytochrome $P_{450}$ isoform is greater than about 10%, as compared to the non-isotopically enriched compound. In other embodiments, the decrease in metabolism of compounds of the invention by the cytochrome $P_{450}$ isoform is greater than about 20%, as compared to the non-isotopically enriched compound. In other embodiments, the decrease in metabolism of compounds of the invention by the cytochrome $P_{450}$ isoform is greater than about 30%, as compared to the non-isotopically enriched compound. In other embodiments, the decrease in metabolism of compounds of the invention by the cytochrome $P_{450}$ isoform is greater than about 40%, as compared to the non-isotopically enriched compound. In other embodiments, the decrease in metabolism of compounds of the invention by the cytochrome $P_{450}$ isoform is greater than about 50%, as compared to the non-isotopically enriched compound.

The metabolic activity of the cytochrome $P_{450}$ isoform is measured by the method described in Example 14 below.

In another embodiment of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect improved biogenic monoamine levels as compared to the non-isotopically enriched compound.

In some embodiments, biogenic monoamine levels are increased by greater than about 5%. In other embodiments, biogenic monoamine levels are increased by greater than about 10%. In other embodiments, biogenic monoamine levels are increased by greater than about 20%. In other embodiments, biogenic monoamine levels are increased by greater than about 30%. In other embodiments, biogenic monoamine levels are increased by greater than about 40%. In other embodiments, biogenic monoamine levels are increased by greater than about 50%.

Biogenic monoamine levels are measured by the methods of Li et al *Rapid Communications in Mass Spectrometry* 2005, 19(14), 1943-1950, which is hereby incorporated by reference in its entirety.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, so as to affect an improved clinical effect as compared to the non-isotopically enriched compound. Examples of improved clinical effects include but are not limited to accelerated rate of healing, accelerated rate of symptom relief, improved patient compliance, and/or reduced substance abuse withdrawal symptomology during the treatment.

In another aspect of the invention, there are provided methods for treating a mammalian subject, particularly a human, suspected of having, or being prone to a disease or condition involving monoamine reuptake, comprising administering to a mammalian subject in need thereof a therapeutically effective amount of a monoamine reuptake inhibitor comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, provided that said compound of Formula 1 contains at least one deuterium atom, and provided that deuterium enrichment in said compound of Formula 1 is at least about 1%.

In some embodiments, disease or condition involving monoamine reuptake is selected from the group consisting of anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, and premature ejaculation.

In another aspect of the invention, there are provided oral multiple unit tablet pharmaceutical compositions comprising a first component and a second component for the treatment of a drug addiction. In some embodiments, the first component comprises at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof. In certain embodiments, the second component comprises one or more opioid antagonists. In some of these embodiments, the opioid antagonist is selected from the group consisting of nalmefene, naloxone, and naltrexone, and the like. In further embodiments, the drug addiction is selected from the group consisting of addiction to tobacco, alcohol, marijuana, and cocaine. In certain embodiments, the first component is separated from the second component by a coating layer covering the first and the second components. Such coating agents are known to those skilled in the art.

In another aspect of the invention, there are provided methods of treating a mammal for a drug addiction comprising administering to the mammal a composition comprising a first component and a second component, where the first component comprises of at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, and the second component comprises one or more opioid antagonists. In some of these embodiments, the opioid antagonist is selected from the group consisting of nalmefene, naloxone, and naltrexone, and the like. In further embodiments, the drug addiction is selected from the group consisting of addiction to tobacco, alcohol, marijuana, and cocaine. In still further embodiments, the first component can elicit an improved clinical effect for the treatment of a drug addiction, as compared to the non-isotopically enriched analog of the first component (e.g., accelerated rate of healing, accelerated rate of symptom relief, improved patient compliance, and/or reduced substance abuse withdrawal symptomatology during the treatment).

In some embodiments, the administering step comprises administering the first component and the second component nearly simultaneously. These embodiments include those in which the two compounds are in the same administrable composition, i.e., a single tablet, pill, or capsule, or a single solution for intravenous injection, or a single drinkable solution, or a single dragee formulation or patch, contains both compounds. The embodiments also include those in which each compound is in a separate administrable composition, but the patient is directed to take the separate compositions nearly simultaneously, i.e., one pill is taken right after the other or that one injection of one compound is made right after the injection of another compound, etc. In some embodiments, a patient is infused with an intravenous formulation of one compound prior to the infusion of an intravenous formulation of the other compound. In these embodiments, the infusion may take some time, such as a few minutes, a half hour, or an hour, or longer. If the two intravenous infusions are done one right after the other, such administration is considered to be nearly simultaneously within the scope of the present disclosure, even though there was a lapse of some time between the start of one infusion and the start of the next infusion.

In other embodiments the administering step comprises administering one of the first component and the second component and then administering the other one of the first component and the second component. In these embodiments, the patient may be administered a composition comprising one of the compounds and then at some time, a few minutes or a few hours, later be administered another composition comprising the other one of the compounds. Also included in these embodiments are those in which the patient is administered a composition comprising one of the compounds on a routine or continuous basis while receiving a composition comprising the other compound occasionally. In further embodiments, the patient may receive both compounds on a routine or continuous basis, such as continuous infusion of the compound through an IV line.

In still another aspect of the invention, there are provided effervescent dosage forms comprising a first component and a second component, wherein the first component is one or more effervescent excipients, and the second component is at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, and optionally one or more pharmaceutically acceptable excipients.

In another aspect of the invention, there are provided extended release pharmaceutical dosage forms comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, a hydrophilic or hydrophobic matrix, a water-soluble separating layer, an enteric coating layer, and optionally one or more pharmaceutically acceptable excipients.

In still another aspect of the invention, there are provided enteric coated pharmaceutical dosage forms comprising at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, a disruptable semi-permeable membrane and one or more swellable substances, wherein the dosage form has an instant inhibitor-releasing part and at least one delayed inhibitor-releasing part, and is capable of giving a discontinuous release of the compound in the form of at least two consecutive pulses separated in time from 0.1 up to 24 hours.

In still another aspect of the invention, there are provided stable pharmaceutical dosage forms for oral administration to mammalian subjects which comprises at least one of the compounds of Formula 1, a single enantiomer of a compound of Formula 1, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer of a compound of Formula 1, a mixture of diastereomers, or a pharmaceutically acceptable salt, solvate, or prodrug thereof, and optionally one or more pharmaceutical adjuvants, enclosed in an intermediate reactive layer comprising a gastric juice-resistant polymeric layered material partially neutralized with alkali and having cation exchange capacity and a gastric juice-resistant outer layer.

Unless otherwise indicated, when a substituent is deemed to be "optionally substituted," it is meant that the substituent is a group that may be substituted with one or more group(s) individually and independently selected from the group consisting of hydrogen, deuterium, alkyl, cycloalkyl, aryl, heteroaryl, heterocyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art examples of which may be found in references such as Greene and Wuts, Protective Groups in Organic Synthesis, 3$^{rd}$ Ed., John Wiley & Sons, New York, N.Y., 1999, which is incorporated by reference herein in its entirety.

The compounds according to this invention may occur as any reasonable tautomer as recognized by one skilled in the art or a mixture of such tautomers. The term "tautomer" or "tautomerism" refers to one of two or more structural isomers that exist in equilibrium and are readily converted from one isomeric form to another. Examples include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention.

The compounds according to this invention may contain one or more asymmetric atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical atoms and therefore include various stereoisomers. All such isomeric forms of these compounds are expressly included in the present invention.

Each stereogenic carbon or sulfur may be of R or S configuration. Although the specific compounds exemplified in this application may be depicted in a particular configuration, compounds having the opposite stereochemistry at any given chiral center or mixtures thereof are also envisioned. When chiral centers are found in the derivatives of this invention, it is to be understood that this invention encompasses all possible stereoisomers.

The terms "optically pure compound" or "optically pure isomer" refers to a single stereoisomer of a chiral compound regardless of the configuration of the said compound.

The term "substantially homogeneous" refers to collections of molecules wherein at least about 80%, preferably at least about 90% and more preferably at least about 95% of the molecules are a single compound or a single stereoisomer thereof, or to collections of molecules wherein at least about 80%, preferably at least about 90% and more preferably at least about 95% of the molecules are fully substituted (e.g., deuterated) at the positions stated.

As used herein, the term "attached" signifies a stable covalent bond, certain preferred points of attachment being apparent to those skilled in the art.

The terms "optional" or "optionally" refer to occurrence or non-occurrence of the subsequently described event or circumstance, and that the description includes instances where said event or circumstance occurs and instances where it does not. In such context, the sentence "optionally substituted alkyl group" means that the alkyl group may or may not be substituted and the description includes both a substituted and an unsubstituted alkyl group.

The term "effective amount" of a compound refers a sufficient amount of the compound that provides a desired effect but with no- or acceptable-toxicity. This amount may vary from subject to subject, depending on the species, age, and physical condition of the subject, the severity of the disease that is being treated, the particular compound used, its mode of administration, and the like. A suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

When used in conjunction with a compound of this invention, the terms "elicit", "eliciting," "modulator", "modulate", "modulating", "regulator", "regulate" or "regulating" the activity refer to a compound that can act as an agonist, an inverse agonist, an inhibitor, or an antagonist of a particular enzyme or receptor, such as for example a serotonin receptor.

The terms "drug", "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, inhalation, intravenous infusion, ocular application, transdermal formulation or by injection.

The term "subject" refers to an animal, preferably a mammal, and most preferably a human, who is the object of treatment, observation or experiment. The mammal may be selected from the group consisting of mice, rats, hamsters, gerbils, rabbits, guinea pigs, dogs, cats, sheep, goats, cows, horses, giraffes, platypuses, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system (animal including human) that is being sought by a researcher, veterinarian, medical doctor or other clinician.

The terms "treating," "treatment," "therapeutic," or "therapy" do not necessarily mean total loss of nociception. Any alleviation of any undesired signs or symptoms of a disease, such as those involving monoamine reuptake, anxiety disorder, generalized anxiety disorder, depression, post-traumatic stress disorder, obsessive-compulsive disorder, panic disorder, hot flashes, senile dementia, migraine, hepatopulmonary syndrome, chronic pain, nociceptive pain, neuropathic pain, painful diabetic retinopathy, bipolar depression, obstructive sleep apnea, psychiatric disorders, premenstrual dysphoric disorder, social phobia, social anxiety disorder, urinary incontinence, anorexia, bulimia nervosa, obesity, ischemia, head injury, calcium overload in brain cells, drug dependence, and/or premature ejaculation, or a subset of these conditions, to any extent can be considered treatment or therapy. Furthermore, treatment may include acts that may worsen the patient's overall feeling of well-being or appearance.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, Lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, D.C., United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids may be used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell or an attraction for an electron-rich reactant and as such would be obvious to one of ordinary skill and knowledge in the art. The definition of "electrophile" includes but is not limited to: hydronium, acylium, Lewis acids, such as for example, boron trifluoride and the like, halogens, such as for example $Br_2$ and the like, carbocations, such as for example tert-butyl cation and the like, diazomethane, trimethylsilyldiazomethane, alkyl halides, such as for example methyl iodide, trideuteromethyl iodide ($CD_3I$), benzyl bromide and the like, alkyl triflates, such as for example methyl triflate and the like, alkyl sulfonates, such as for example ethyl toluenesulfonate, butyl methanesulfonate, dimethylsulfate, hexadeuterodimethylsulfate (($CD_3$)$_2SO_4$) and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-toluenesulfonyl chloride and the like, silyl halides, such as for example trimethylsilyl chloride, tert-butyldimethylsilyl chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" (LG) refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of an atom, such as for example, hydrogen, carbon, nitrogen, sulfur, phosphorus and the like in the starting material by either adding an oxygen to this atom or removing an electron from this atom and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of an atom in the starting material by either adding a hydrogen to this atom, or adding an electron to this atom, or by removing an oxygen from this atom and as such would be obvious to one of ordinary skill and knowledge in the art. The definition of "reducing reagent" includes but is not limited to: borane-dimethyl sulfide complex, 9-borabicyclo[3.3.1.]nonane (9-BBN), catechol borane, lithium borohydride, lithium borodeuteride, sodium borohydride, sodium borodeuteride, sodium borohydride-methanol complex, potassium borohydride, sodium hydroxyborohydride, lithium triethylborohydride, lithium n-butylborohydride, sodium cyanoborohydride, sodium cyanoborodeuteride, calcium (II) borohydride, lithium aluminum hydride, lithium aluminum deuteride, diisobutylAluminum hydride, n-butyl-diisobutylaluminum hydride, Sodium bis-methoxyethoxyAluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl) carbodiimide (EDCI), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O—(N-succinimidyl)-1,1,3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl)ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;

b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (trityl), α-naphthyldiphenylmethyl, (4-methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,i]fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)R$_{30}$, where R$_{30}$ is selected from the group consisting of alkyl, substituted alkyl, aryl and more specifically R$_{30}$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

e) —C(O)OR$_{30}$, where R$_{30}$ is selected from the group consisting of alkyl, substituted alkyl, aryl and more specifically R$_{30}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like. Other examples of hydroxyl protecting groups are given in Greene and Wutts, above.

The definition of "amino protecting group" includes but is not limited to:

2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl and the like;

—C(O)OR$_{30}$, where R$_{30}$ is selected from the group consisting of alkyl, substituted alkyl, aryl and more specifically R$_{30}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-Isopropylallyl, cinnamyl. 4-nitrocinnamyl, 3-(3-pyridyl)prop-2-enyl, 8-quinolyl, N-Hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like. Other examples of amino protecting groups are given in Greene and Wutts, above.

The definition of "carboxyl protecting group" includes but is not limited to:

2-N-(morpholino)ethyl, choline, methyl, methoxyethyl, 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2-pyridyl)ethyl, 2-(p-methoxyphenyl)ethyl, 2-(diphenylphosphino)ethyl, 1-methyl-1-phenyl ethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{N-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like. Other examples of carboxyl protecting groups are given in Greene and Wutts, above.

The definition of "thiol protecting group" includes but is not limited to:

I. Alkyl, benzyl, 4-methoxybenzyl, 2-hydroxybenzyl, 4-hydroxybenzyl, 2-acetoxybenzyl, 4-acetoxybenzyl, 4-nitrobenzyl, 2,4,6-trimethylbenzyl, 2,4,6-trimethoxybenzyl, 4-picolyl, 2-quinolinylmethyl, 2-picolyl n-oxide, 9-anthrylmethyl, 9-fluorenylmethyl, xanthenyl, ferrocenylmethyl and the like;

II. Diphenylmethyl, bis(4-methoxyphenyl)methyl, 5-dibenzosuberyl, triphenylmethyl, diphenyl-4-pyridylmethyl, phenyl, 2,4-dinitrophenyl, tert-butyl, 1-adamantyl and the like;

III. Methoxymethyl, isobutoxymethyl, benzyloxymethyl, 2-tetrahydropyranyl, benzylthiomethyl, phenylthiomethyl, acetamidomethyl, trimethylacetamidomethyl, benzamidomethyl, allyloxycarbonylaminomethyl, phenylacetamidomethyl, phthalimidomethyl, acetyl, carboxy-, cyanomethyl and the like;

IV. (2-nitro-1-phenyl)ethyl, 2-(2,4-dinitrophenyl)ethyl, 2-(4'-pyridyl)ethyl, 2-cyanoethyl, 2-(trimethylsilyl)ethyl, 2,2-bis(carboethoxy)ethyl, 1-(3-nitrophenyl)-2-benzoylethyl, 2-phenylsulfonylethyl, 1-(4-methylphenylsulfonyl)-2-methylpro4-2-yl and the like;

V. Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

VI. Benzoyl, trifluoroacetyl, N-[[(4-biphenylyl)isopropoxy]carbonyl]-N-methyl-γ-aminothiobutyrate, N-(t-butoxycarbonyl)-N-methyl-γ-aminothiobutyrate and the like;

VII. 2,2,2-Trichloroethoxycarbonyl, tert-butoxycarbonyl, benzyloxycarbonyl, 4-methoxybenzyloxycarbonyl and the like;

VIII. N-(Ethylamino)carbonyl, N-(methoxymethylamino)carbonyl and the like;

IX. Ethylthio, tert-butylthio, phenylthio, substituted phenylthio and the like;

X. (Dimethylphosphino)thioyl, (diphenylphosphino)thioyl and the like;

XI. Sulfonate, alkyloxycarbonylthio, benzyloxycarbonylthio, 3-nitro-2-pyridinethio and the like;

XII. Tricarbonyl[1,2,3,4,5-η]-2,4-cyclohexadien-1-yl]-iron(1+) and the like. Other examples of thiol protecting groups are given in Greene and Wutts, above.

The term "amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101(Peptide and Protein Drug Analysis), 191-205; Pojitkov, A. E. Journal of Molecular Catalysis B: Enzymatic (2000), 10(1-3), 47-55; Ager, D. J. Speciality Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of beta.-Lactam antibiotics," Pharm. Biotech. 11, 345-365; Gaignault et al. (1996) "Designing Prodrugs and Bioprecursors I. Carrier Prodrugs," Pract. Med. Chem. 671-696; Asghamejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenyloin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

In light of the purposes described for the present invention, all references to reagents ordinarily containing hydrogens, hydrides, or protons may include partially or fully deuterated versions (containing deuterium, deuteride, or deuterium) as required to affect transformation to the improved drug substances outlined herein.

The term "halogen", "halide" or "halo" includes fluorine, chlorine, bromine, and iodine.

The terms "alkyl" and "substituted alkyl" are interchangeable and include substituted, optionally substituted and unsubstituted $C_1$-$C_{10}$ straight chain saturated aliphatic hydrocarbon groups, substituted, optionally substituted and unsubstituted $C_2$-$C_{10}$ straight chain unsaturated aliphatic hydrocarbon groups, substituted, optionally substituted and unsubstituted $C_2$-$C_{10}$ branched saturated aliphatic hydrocarbon groups, substituted and unsubstituted $C_2$-$C_{10}$ branched unsaturated aliphatic hydrocarbon groups, substituted, optionally substituted and unsubstituted $C_3$-$C_8$ cyclic saturated aliphatic hydrocarbon groups, substituted, optionally substituted and unsubstituted $C_5$-$C_8$ cyclic unsaturated aliphatic hydrocarbon groups having the specified number of carbon atoms. For example, the definition of "alkyl" shall include but is not limited to: methyl (Me), trideuteromethyl (—$CD_3$), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group consisting of hydrogen, deuterium, halogen, —OH, —SH, —$NH_2$, —CN, —$NO_2$, =O, =$CH_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$alkylamino, N-aryl-N—$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, —$C_{0-10}$alkylCOOR$_{31}$, and —$CO_{0-10}$alkylCONR$_{32}$R$_{33}$ wherein R$_{31}$, R$_{32}$ and R$_{33}$ are independently selected from the group consisting of hydrogen, deuterium, alkyl, aryl, or R$_{32}$ and R$_{33}$ are taken together with the nitrogen to which they are attached forming a saturated cyclic or unsaturated cyclic system containing 3 to 8 carbon atoms with at least one substituent as defined herein.

In light of the purposes described for the present invention, all references to "alkyl" groups or any groups ordinarily containing C—H bonds may include partially or fully deuterated versions as required to affect the improvements outlined herein.

The term "alkyloxy" (e.g. methoxy, ethoxy, propyloxy, allyloxy, cyclohexyloxy) represents a substituted or unsubstituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkyloxycarbonyl" (e.g. methoxycarbonyl, ethoxycarbonyl, tert-butoxycarbonyl, allyloxycarbonyl) represents a substituted or unsubstituted alkyloxy group as defined above having the indicated number of carbon atoms attached through a carbonyl bridge.

The term "alkylthio" (e.g. methylthio, ethylthio, propylthio, cyclohexenylthio and the like) represents a substituted or unsubstituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of carbon atoms attached through an amine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylaminoalkyl" represents an alkylamino group attached through a substituted or unsubstituted alkyl group as defined above having the indicated number of carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of carbon atoms attached through a nitrogen atom of a hydrazine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylhydrazinoalkyl" represents an alkylhydrazino group attached through a substituted or unsubstituted alkyl group as defined above having the indicated number of carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of carbon atoms attached through a carbonyl group. The term "alkylcarbonylalkyl" represents an alkylcarbonyl group attached through a substituted or unsubstituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, or polysubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphthyl and the like). The aryl substituents are independently selected from the group consisting of hydrogen, deuterium, halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{31}$, and —$C_{0-10}$alkylCONR$_{32}$R$_{33}$ wherein R$_{31}$, R$_{32}$ and R$_{33}$ are independently selected from the group consisting of hydrogen, deuterium, alkyl, aryl or R$_{32}$ and R$_{33}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, pentadeuterophenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl)propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through a substituted or unsubstituted alkyl group as defined above having the indicated number of carbon atoms.

The term "aryloxycarbonyl" (e.g. phenoxycarbonyl, naphthoxycarbonyl) represents a substituted or unsubstituted aryloxy group as defined above having the indicated number of carbon atoms attached through a carbonyl bridge.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through a substituted or unsubstituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through a substituted or unsubstituted alkyl group as defined above having the indicated number of carbon atoms. The term "arylalkylamino" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of carbon atoms attached through a hydrazine bridge. The term "arylhydrazinoalkyl" represents an arylhydrazino group attached through a substituted or unsubstituted alkyl group as defined above having the indicated number of carbon atoms. The term "arylalkylhydrazino" represents an aryl group attached through an alkylhydrazino group as defined above having the indicated number of carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of carbon atoms independently attached through an amine atom of a hydrazine bridge.

The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with a substituted or unsubstituted alkyl or aryl group. The term "arylcarbonylaminoalkyl" represents an arylcarbonylamino group attached through a substituted or unsubstituted alkyl group as defined above having the indicated number of carbon atoms. The Nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 13 carbon atoms and from 1 to 10 hetero atoms selected from the group consisting of nitrogen, sulfur, and oxygen, within the ring. The heteroaryl groups in this invention can be optionally substituted with 1 to 10 substituents selected from the group consisting of: hydrogen, deuterium, halogen, —OH, —SH, —CN, —NO$_2$, trihalomethyl, hydroxypyronyl, $C_{1-10}$alkyl, aryl$C_{0-10}$ alkyl, $C_{0-10}$alkyloxy$C_{0-10}$alkyl, aryl$C_{0-10}$alkyloxy$C_{0-10}$ alkyl, $C_{0-10}$alkylthio$C_{0-0}$alkyl, aryl$C_{0-10}$alkylthio$C_{0-10}$ alkyl, $CO_{0-10}$alkylamino$C_{0-10}$alkyl, aryl$C_{0-10}$ alkylamino$C_{0-10}$alkyl, N-aryl-N—$C_{0-10}$alkylamino$C_{0-10}$ alkyl, $C_{1-10}$alkylcarbonyl$C_{0-10}$alkyl, aryl$C_{0-10}$ alkylcarbonyl$C_{0-10}$alkyl, $C_{1-10}$alkylcarboxy$C_{0-10}$alkyl, aryl$C_{0-10}$alkylcarboxy$C_{0-10}$ alkyl, $C_{1-10}$alkylcarbonylamino$C_{0-10}$alkyl, aryl$C_{0-10}$alkylcarbonylamino$C_{0-10}$alkyl, —$C_{0-10}$ alkylCOOR$_{31}$, and —$C_{0-10}$ alkylCONR$_{32}$R$_{33}$ wherein R$_{31}$, R$_{32}$ and R$_{33}$ are independently selected from the group consisting of hydrogen, deuterium, alkyl, aryl, or R$_{32}$ and R$_{33}$ are taken together with the nitrogen to which they are attached forming a saturated cyclic or unsaturated cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, deuterobenzimidazolyl, dideuterobenzimidazolyl, trideuterobenzimidazolyl, tetradeuterobenzimidazolyl, pyridyl, deuteropyridyl, dideuteropyridyl, trideuteropyridyl, tetradeuteropyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, 5-methoxy-1H-benzoimidazolyl, 3-ethylpyridyl, 5-methyl-2-phenyl-oxazolyl, 5-methyl-2-thiophen-2-yl-oxazolyl, 2-furan-2-yl-5-methyl-oxazolyl, 3-methyl-3H-quinazolin-4-one, 4-methyl-2H-phthalazin-1-one, 2-ethyl-6-methyl-3H-pyrimidin-4-one, 5-methoxy-3-methyl-3H-imidazo[4,5-b]pyridine and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, and polysubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl, DBU, and the like).

The saturated heterocyclic substituents are independently selected from the group consisting of halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{1-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$ alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl $C_{0-10}$ alkylcarbonylamino$C_{0-10}$alkyl, —$C_{0-10}$alkylCOOR$_{31}$, and —$C_{0-10}$alkylCONR$_{32}$R$_{33}$ wherein R$_{31}$, R$_{32}$ and R$_{33}$ are independently selected from the group consisting of hydrogen, deuterium, alkyl, aryl, or R$_{32}$ and R$_{33}$ are taken together with the nitrogen to which they are attached forming a saturated cyclic or unsaturated cyclic system containing 3 to 8 carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded carbon and which would be obvious to one of ordinary skill and knowledge in the art. The definition of alpha-beta-unsaturated carbonyl includes but is not limited to acrolein, methyl vinyl ketone, and the like.

The term "acetal" refers to a molecule that contains a carbon atom $C_1$ that is directly attached to a hydrogen atom ($H_1$), a substituted carbon atom ($C_2$) and two oxygen atoms ($O_1$ and $O_2$). These oxygen atoms are in turn attached to other substituted carbon atoms ($C_3$ and $C_4$), which would be obvious to one of ordinary skill and knowledge in the art. The definition of acetal includes but is not limited to 1,1-dimethoxypropane, 1,1-bis-allyloxybutane and the like.

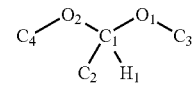

The term "cyclic acetal" refers to an acetal as defined above where $C_3$ and $C_4$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2-methyl-[1,3]dioxolane, 2-ethyl-[1,3]dioxane, 2-phenyl-[1,3]dioxane, 2-phenyl-hexahydro-pyrano[3,2-d][1,3]dioxine and the like.

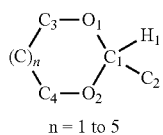

n = 1 to 5

The term "ketal" refers to a molecule that contains a carbon atom $C_1$ that is directly attached to two substituted carbon atom ($C_2$ and $C_3$) and two oxygen atoms ($O_1$ and $O_2$). These oxygen atoms are in turn attached to other substituted carbon atoms ($C_4$ and $C_5$), which would be obvious to one of ordinary skill and knowledge in the art. The definition of acetal includes but is not limited to 2,2-dimethoxy-butane, 3,3-diethoxy-pentane and the like.

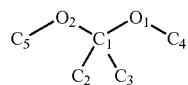

The term "cyclic ketal" refers to a ketal as defined above where $C_4$ and $C_5$, together with the oxygen atoms to which they are attached, combine thru an alkyl bridge to form a 5- to 10-membered ring, which would be obvious to one of ordinary skill and knowledge in the art. The definition of cyclic acetal includes but is not limited to 2,2,4,5-tetramethyl-[1,3]dioxolane, 2,2-diethyl-[1,3]dioxepane, 2,2-dimethyl-hexahydro-pyrano[3,2-d][1,3]dioxine and the like.

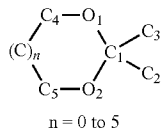

n = 0 to 5

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines a solution, typically one that is aqueous or partially aqueous, that dissolves chemical compounds of interest and may stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

Before the present compounds, compositions and methods are disclosed and described, it is to be understood that aspects of the present invention are not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It is also noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds; reference to "a pharmaceutical carrier" includes mixtures of two or more such carriers, and the like.

Certain pharmaceutically acceptable salts of the invention are prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, Aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water or D$_2$O, alone or in combination with an inert, water-miscible organic solvent, or in organic solvent alone, at a temperature of from about 0° C. to about 100° C., preferably at room temperature. The molar ratio of compounds of structural Formula 1 to base used is chosen to provide the ratio desired for any particular salts. For preparing, for example, the ammonium salts of the starting material, compounds of Formula 1 can be treated with approximately one equivalent of the pharmaceutically acceptable base to yield a neutral salt. When calcium salts are prepared, approximately one-half a molar equivalent of base is used to yield a neutral salt, while for aluminum salts, approximately one-third a molar equivalent of base will be used.

The compounds of the invention may be conveniently formulated into pharmaceutical compositions composed of one or more of the compounds together with a pharmaceutically acceptable carrier as described in Remington's Pharmaceutical Sciences, latest edition, by E. W. Martin (Mack Publ. Co., Easton Pa.).

The compounds of the invention may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. The dosage will be in the range of about 1 microgram per kilogram per day to 100 milligram per kilogram per day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels and the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents and the like.

For solid compositions, conventional non-toxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable-compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Wherever required, flavoring, preserving, suspending, thickening, or emulsifying agents may also be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, as emulsions, or as sustained release delivery system.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one aspect, the transdermal delivery agent can be DMSO. Transdermal delivery systems can include, such as for example, patches.

Pharmaceutical compositions containing the compounds of the invention as an active ingredient can take the form of tablets, capsules, powders, suspensions, solutions, emulsions as well as salves and creams, and can be used for parenteral (intravenous, intradermal, intramuscular, intrathecal etc.) injections, infiltration, topical application, central injection at spinal cord, oral, rectal, intravaginal and intranasal administering or for local application. Such compositions can be prepared by combining the active ingredient(s) with pharmaceutically acceptable excipients normally used for this purpose. Such excipients can comprise aqueous and non-aqueous solvents, stabilizers, suspension agents, dispersing agents, moisturizers and the like, and will be known to the skilled person in the pharmaceutical field. The composition may further contain likewise suitable additives such as for instance polyethylene glycols and, if necessary, colorants, fragrances and the like.

The pharmaceutical compositions will preferably contain at least about 0.1 volume % by weight of the active ingredient. The actual concentration will depend on the human subject and the chosen administering route. In general this concentration will lie between about 0.1 and about 100% for the above applications and indications. The dose of the active ingredient to be administered can further vary between about 1 microgram and about 100 milligram per kilogram body weight per day, preferably between about 1 microgram and 50 milligram per kilogram body weight per day, and most preferably between about 1 microgram and 20 milligram per kilogram body weight per day.

The desired dose is preferably presented in the form of one, two, three, four, five, six or more sub-doses that are administered at appropriate intervals per day. The dose or sub-doses can be administered in the form of dosage units containing for instance from 0.5 to 1500 milligram, preferably from 0.5 to 200 milligram and most preferably from 0.5 to 40 milligram active constituent per dosage unit, and if the condition of the patient requires the dose can, by way of alternative, be administered as a continuous infusion.

EXAMPLES

As used herein, and unless otherwise indicated, the following abbreviations have the following meanings: Me refers to methyl ($CH_3$—), Et refers to ethyl ($CH_3CH_2$—), i-Pr refers to isopropyl (($CH_3$)$_2$$CH_2$—), t-Bu or tert-butyl refers to tertiary butyl (($CH_3$)$_3$CH—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to tert-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), $D_2O$ refers to deuterium oxide, DMF refers to N,N-dimethylformamide, DCM refers to dichloromethane (CH₂Cl₂), THF refers to tetrahydrofuran, EtOAc refers to ethyl acetate, Et₂O refers to diethyl ether, MeCN refers to acetonitrile (CH₃CN), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCI refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)₂NEt or DIEA or Hunig's base refers to N,N-diethylisopropylamine, DBU refers to 1,8-Diazabicyclo[5.4.0]undec-7-ene, (DHQ)₂AQN refers to dihydroquinine anthraquinone-1,4-diyl diether, (DHQ)₂PHAL refers to dihydroquinine phthalazine-1,4-diyl diether, (DHQ)₂PYR refers to dihydroquinine 2,5-diphenyl-4,6-pyrimidinediyl diether, (DHQD)₂AQN refers to dihydroquinidine anthraquinone-1,4-diyl diether, (DHQD)₂PHAL refers to dihydroquinidine phthalazine-1,4-diyl diether, (DHQD)₂PYR refers to dihydroquinidine 2,5-diphenyl-4,6-pyrimidinediyl diether, LDA refers to lithium diisopropylamide, LiTMP refers to lithium 2,2,6,6-tetramethylpiperidinamide, n-BuLi refers to n-butyl lithium, t-BuLi refers to tert-butyl lithium, IBA refers to 1-hydroxy-1,2-benziodoxol-3(1H)-one 1-oxide, OsO₄ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, Ac₂O refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, ZnCl₂ refers to zinc (II) dichloride, BF₃ refers to boron trifluoride, Y(OTf)₂ refers to yttrium (III) trifluoromethanesulfonate, Cu(BF₄)₂ refers to copper (II) tetrafluoroborate, LAH refers to lithium aluminum hydride (LiAlH₄), LAD refers to lithium aluminum deuteride, NaHCO₃ refers to Sodium bicarbonate, K₂CO₃ refers to Potassium carbonate, NaOH refers to sodium hydroxide, KOH refers to potassium hydroxide, LiOH refers to lithium hydroxide, HCl refers to hydrochloric acid, H₂SO₄ refers to sulfuric acid, MgSO₄ refers to magnesium sulfate, and Na₂SO₄ refers to sodium sulfate. ¹H NMR refers to proton nuclear magnetic resonance, ¹³C NMR refers to carbon-13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, $R_f$ refers to retention factor, $R_t$ refers to retention time, GC refers to gas chromatography, min is minutes, h is hours, rt or RT is room or ambient temperature, g is grams, mg is milligrams, kg is kilograms, L is liters, mL is milliliters, mol is moles and mmol is millimoles.

For all of the following examples, standard work-up and purification methods can be utilized and will be obvious to those skilled in the art. Synthetic methodologies that make up the invention are shown in Scheme 1. This scheme is just one of many available literature preparative routes and is intended to exemplify the applicable chemistry through the use of specific examples and is not indicative of the scope of the invention.

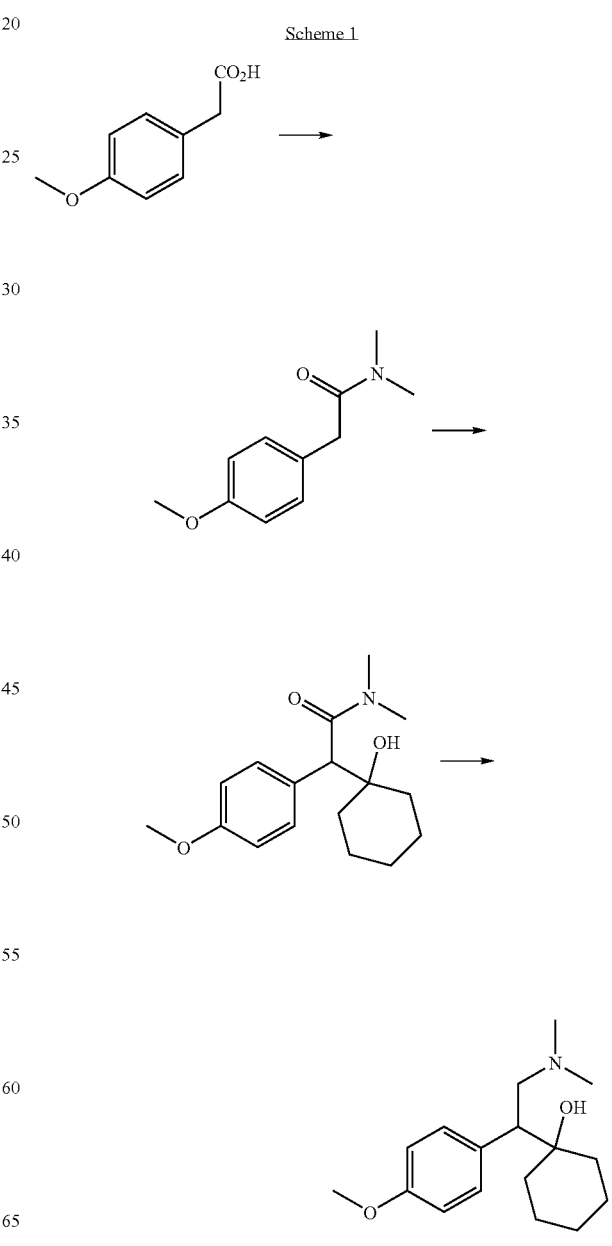

Scheme 1

Examples

The following non-limiting examples illustrate the inventors' preferred methods for carrying out the process of the invention.

Example 1

$d_9$-2-(4-Methoxyphenyl)-acetic acid

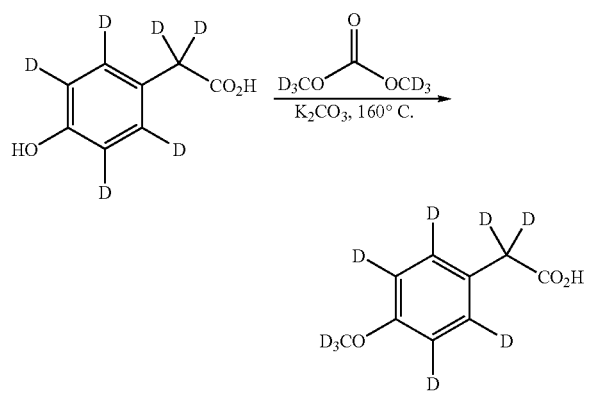

$d_9$-(4-Methoxyphenyl)-acetic acid can be prepared according to known literature procedures Ouk et al., *Green Chemistry*, 2002, 4(5), 431-435, which is hereby incorporated by reference in its entirety, by reacting $d_6$-(4-hydroxyphenyl)-acetic acid (1 equiv, Cambridge Isotopes Laboratories), $K_2CO_3$ (0.04 equiv) and $d_6$-carbonic acid dimethyl ester (1.25 equiv, Cambridge Isotopes Laboratories) at 160° C. until completion.

Example 2

$d_{15}$-2-(4-Methoxyphenyl)-N,N-dimethyl-acetamide

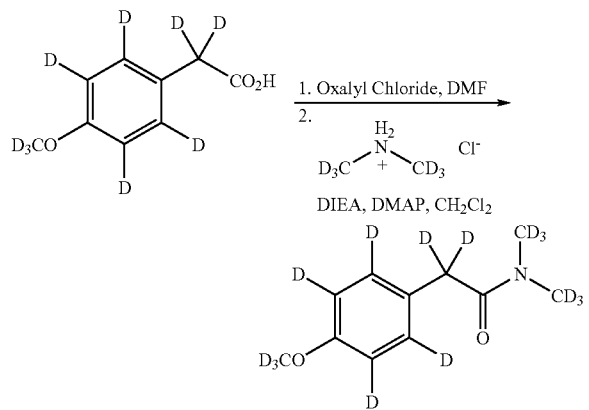

The title compound is prepared according to the procedure described in Yardley et al, *Journal of Medicinal Chemistry* 1990, 33(10), 2899-2905, which is hereby incorporated by reference in its entirety. A solution of $d_9$-(4-methoxyphenyl)-acetic acid (1 equiv) in methylene chloride is treated with oxalyl chloride (1.22 equiv) and DMF (catalytic amount) and then stirred at room temperature until all acid is converted to the acid chloride. The solvent is removed under reduced pressure and the residue is taken up in methylene chloride and treated with $d_6$-dimethylamine hydrochloride (1 equiv, Cambridge Isotopes Laboratories), ethyl diisopropylamine (2.1 equiv), and DMAP (0.2 equiv). The mixture is stirred overnight, the solvent is removed under reduced pressure and the crude residue is purified by silica gel column chromatography.

Example 3

$d_{24}$-2-(1-Hydroxycyclohexyl)-2-(4-methoxyphenyl)-N,N-dimethyl-acetamide

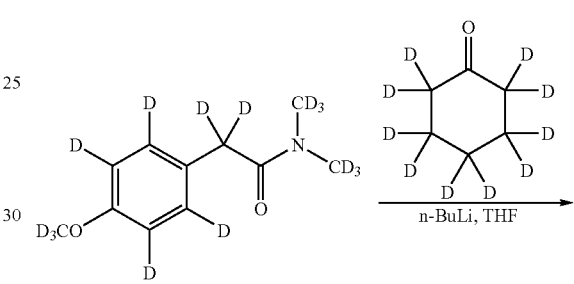

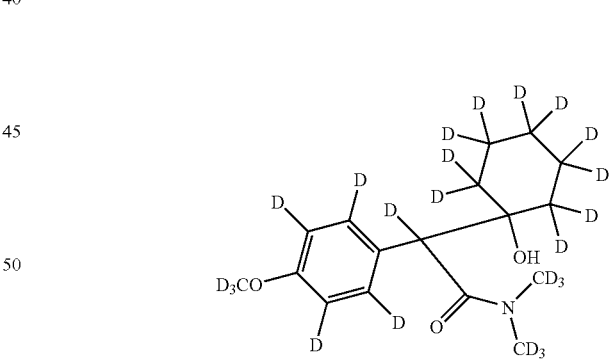

The title compound is prepared according to the procedure described in Yardley et al., *Journal of Medicinal Chemistry* 1990, 33(10), 2899-2905. A solution of $d_{15}$-2-(4-methoxyphenyl)-N,N-dimethyl-acetamide (1 equiv) in THF is treated with n-butyllithium (1 equiv) at −78° C. The mixture is stirred for 90 minutes at −78° C.; a THF solution of $d_{10}$-cyclohexanone (1.2 equiv, Sigma-Aldrich) is added, and stirring is maintained until completion. The reaction is quenched by addition of $D_2O$ (2 equiv), the mixture is warmed to room temperature and the solvent is removed under reduced pressure and the crude residue is purified by silica gel column chromatography.

Example 4 d$_{26}$-1-[2-Dimethylamino-1-(4-methoxyphenyl)-ethyl]-cyclohexanol

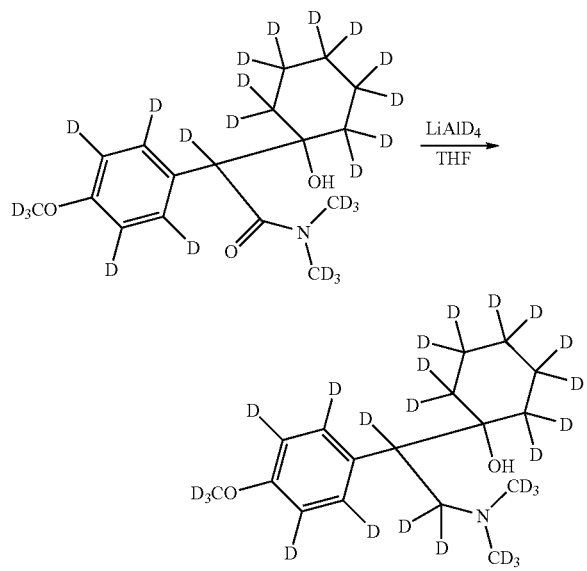

The title compound is prepared according to the procedure described in Yardley et al., *Journal of Medicinal Chemistry* 1990, 33(10), 2899-2905. d$_{24}$-2-(1-Hydroxycyclohexyl)-2-(4-methoxyphenyl)-N,N-dimethyl-acetamide (1 equiv) in THF is added dropwise to a mixture of lithium aluminum deuteride (1.6 equiv) at 0° C. and stirred until completion. The reaction is quenched with D$_2$O, and worked up under standard conditions known to one skilled in the art. The mixture is then filtered and the precipitate is washed several times with THF. The combined filtrates are evaporated, and the residue is recrystallized from a suitable solvent.

Example 5 d$_3$-(4-Methoxyphenyl)-acetonitrile

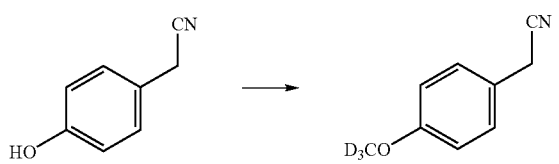

d$_3$-Iodomethane (8.70 g, 60 mmol) was added to a stirred solution of (4-hydroxyphenyl)-acetonitrile (4.50 g, 30 mmol) in acetone (30 mL) containing potassium carbonate (6.21 g, 45 mmol) at ambient temperature, and the mixture was heated at reflux overnight, cooled to ambient temperature, filtered, and concentrated to give the crude product, which was purified by flash chromatography using hexanes-ethyl acetate to afford the desired product, d$_3$-(4-methoxyphenyl)-acetonitrile, as a light yellow oil.

Yield: 3.99 g (89%). $^1$H-NMR (CDCl$_3$) δ ppm: 3.67 (s, 2H), 6.88 (d, 2H, J=8.7 Hz), 7.22 (d, 2H, J=8.7 Hz).

Example 5 d$_3$-(1-Hydroxycyclohexyl)-(4-methoxyphenyl)-acetonitrile

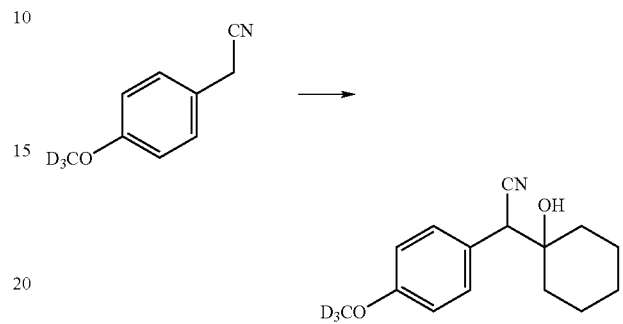

Tetra-n-butyl ammonium hydrogen sulfate (0.10 g, 0.29 mmol) and 2N NaOH (1.2 mL) were added sequentially to a vigorously stirred d$_3$-(4-methoxyphenyl)-acetonitrile (0.85 g, 5.66 mmol) at 0° C., and stirring was maintained for 30 minutes. Cyclohexanone (0.67 g, 6.8 mmol) was added to this mixture at 0-5° C. over 10 minute. The reaction mixture was allowed to warm to ambient temperature and vigorous stirring was continued for an additional 1 hour. The white precipitate was filtered and washed with water and hexanes to afford the desired product, d$_3$-(1-hydroxycyclohexyl)-(4-methoxyphenyl)-acetonitrile, as a white solid.

Yield: 1.28 g (91%). $^1$H-NMR (CDCl$_3$) δ ppm: 1.05-1.80 (m, 10H), 3.73 (s, 1H), 6.90 (d, 2H, J=8.7 Hz), 7.27 (d, 2H, J=8.7 Hz).

Example 6 d$_3$-1-[2-Amino-1-(4-methoxyphenyl)-ethyl]-cyclohexanol

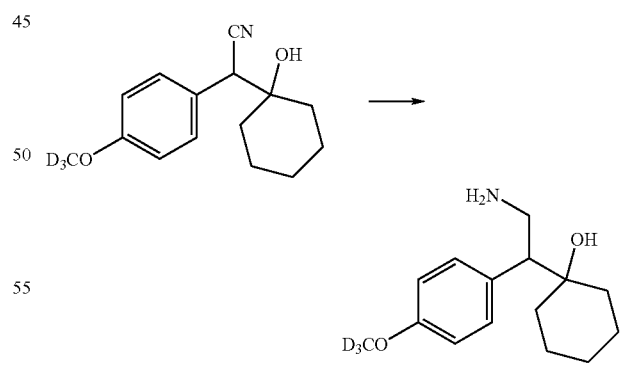

d$_3$-(1-Hydroxycyclohexyl)-(4-methoxyphenyl)-acetonitrile (400.0 mg, 1.61 mmol) was reduced on an H-Cube™ continuous-flow hydrogenation reactor (Thales Nanotechnology, Budapest, Hungary) equipped with a Raney Ni catalyst cartridge (eluent: 2.0M ammonia in methanol, flow rate: 1 mL/min, temperature: 80° C., pressure: 80 bar) to yield the desired product, d$_3$-1-[2-amino-1-(4-methoxyphenyl)-ethyl]-cyclohexanol, as a clear colorless oil.

Yield: 280 mg (69%). $^1$H-NMR (CDCl$_3$) δ ppm: 1.05-1.80 (m, 10H), 2.59 (br s, 2H), 2.68 (t, 1H, 6.9 Hz), 3.21 (m, 2H), 6.83 (d, 2H, J=9.0 Hz), 7.17 (d, 2H, J=9.0 Hz).

Example 7 d$_3$-1-[2-Dimethylamino-1-(4-methoxyphenyl)-ethyl]-cyclohexanol (d$_3$-venlafaxine)

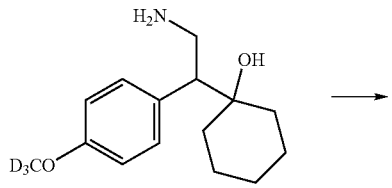

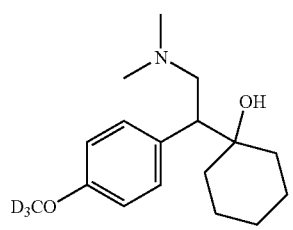

d$_3$-1-[2-Amino-1-(4-methoxyphenyl)-ethyl]-cyclohexanol (207 mg, 0.82 mmol), 37% aqueous formaldehyde (0.3 mL), formic acid (0.3 mL) and water (2 mL) were stirred at 80-90° C. for 12 hours, concentrated in vacuo to a volume of 1.5 mL, made basic by the dropwise addition of aqueous 20% sodium hydroxide, and extracted with ethyl acetate. The combined organic layers were washed with brine, dried (Na$_2$SO$_4$), filtered and concentrated in vacuo to give a crude residue which was purified by silica gel chromatography (ethyl acetate-methanol-ammonium hydroxide) to give the desired product, d$_3$-1-[2-dimethylamino-1-(4-methoxyphenyl)-ethyl]-cyclohexanol.

Yield: 24.4 mg (11%). $^1$H-NMR (methanol-d$_4$) δ ppm: 0.84-1.54 (m, 10 H), 2.42 (s, 6H), 2.84-2.92 (m, 2H), 3.26-3.36 (m, 1H), 6.87 (d, 2H), 7.18 (d, 2H).

Example 8 d$_9$-1-[2-Dimethylamino-1-(4-methoxyphenyl)-ethyl]-cyclohexanol (d$_9$-venlafaxine)

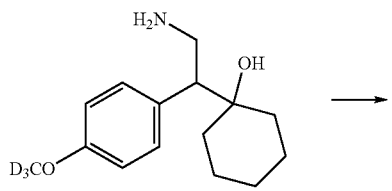

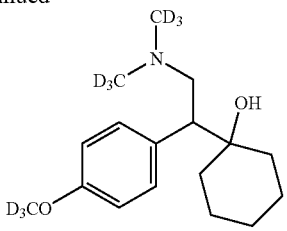

A solution of d$_3$-1-[2-amino-1-(4-methoxyphenyl)-ethyl]-cyclohexanol (0.126 g, 0.5 mmol), d$_2$-formic acid (0.3 mL), and d$_2$-formadhyde (20 wt % in D$_2$O, 0.25 mL) in D$_2$O (1.5 mL) was heated at 100° C. for 16 hours, cooled to ambient temperature, diluted with water (5 mL), neutralized with 35% aqueous ammonia, and extracted with ethyl acetate. The combined organic layers were dried over sodium sulfate and concentrated under reduced pressure to yield a crude residue which was purified by flash chromatography (ethyl acetate-methanol-NH$_4$OH) to give the desired product, d$_9$-1-[2-methylamino-1-(4-methoxyphenyl)-ethyl]-cyclohexanol, as a light yellow semi-solid.

Yield: 0.024 g (20%). $^1$H-NMR (CDCl$_3$) δ ppm: 0.78-1.80 (m, 10H), 2.33 (dd, 1H, J=12.0, 3.3 Hz), 2.96 (dd, 1H, J=12.0, 3.3 Hz), 3.31 (t, 1H, J=12.0 Hz), 6.81 (d, 2H, J=9.0 Hz), 7.17 (d, 2H, J=9.0 Hz). MS (m/z): 287 (M+1).

Example 9 d$_{14}$-(1-Hydroxycyclohexyl)-(4-methoxyphenyl)-acetonitrile

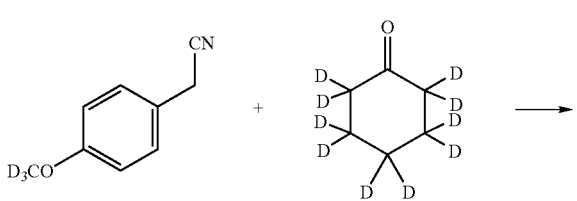

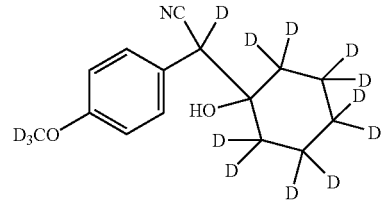

The title compound was prepared as in Example 5 by substituting d$_{10}$-cyclohexanone (Sigma-Aldrich) for cyclohexanone and 2N NaOD in D$_2$O for 2N NaOH in water. The final product was purified by recrystallization from ethyl acetate-hexanes.

Yield (60%). $^1$H-NMR (CDCl$_3$) δ ppm: 1.60 (br s, 1H), 6.90 (d, 2H, J=8.4 Hz), 7.26 (d, 2H, J=8.4 Hz).

Example 10

$d_{14}$-1-[2-Amino-1-(4-methoxyphenyl)-ethyl]-cyclohexanol

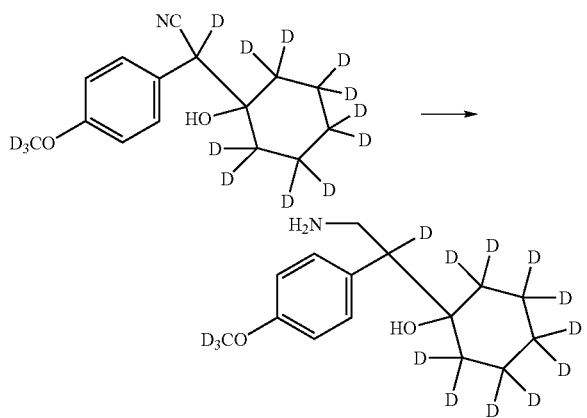

$d_{14}$-(1-Hydroxycyclohexyl)-(4-methoxyphenyl)-acetonitrile (570.0 mg, 2.21 mmol) was reduced on an H-Cube™ continuous-flow hydrogenation reactor (Thales Nanotechnology, Budapest, Hungary) equipped with a Raney Ni catalyst cartridge (eluent: 2.0M ammonia in methanol, flow rate: 1 mL/min, temperature: 80° C., pressure: 80 bar) to yield the desired product, $d_{14}$-1-[2-amino-1-(4-methoxyphenyl)-ethyl]-cyclohexanol, as a clear colorless oil.

Yield: 530 mg (92%). $^1$H-NMR (CDCl$_3$) δ ppm: 2.62 (br s, 3H), 3.21 (dd, 2H), 6.83 (d, 2H), 7.17 (d, 2H).

Example 11

$d_{14}$-1-[2-Dimethylamino-1-(4-methoxyphenyl)-ethyl]-cyclohexanol ($d_{14}$-venlafaxine)

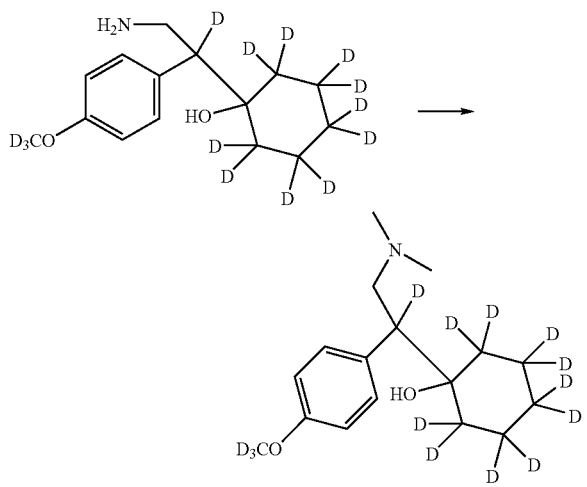

A solution of $d_{14}$-1-[2-amino-1-(4-methoxyphenyl)-ethyl]-cyclohexanol (257.0 mg, 0.98 mmol), formic acid (0.334 mL), and formaldehyde (37% in water, 0.146 mL) in water (2.32 mL) was stirred at room temperature for 45 minutes. Formaldehyde (37% in water, 0.146 mL) was added and the mixture was heated to reflux for 17 hours, cooled to room temperature, washed with ethyl acetate, made basic with 20% aqueous sodium hydroxide and extracted with ethyl acetate. The combined organic fractions were washed with brine, dried (Na$_2$SO$_4$), filtered and concentrated in vacuo to give a crude residue which was purified by column chromatography (ethyl acetate-methanol-ammonium hydroxide) to give the desired product, $d_{14}$-1-[2-dimethylamino-1-(4-methoxyphenyl)-ethyl]-cyclohexanol, as a clear colorless oil.

Yield: 154.4 mg (54%), $^1$H-NMR (methanol-d$_4$) δ ppm: 2.25 (s, 6H), 2.55 (d, 1H), 3.14 (d, 1H), 6.84 (d, 2H), 7.13 (d, 2H).

Example 12

$d_{20}$-1-[2-Dimethylamino-1-(4-methoxyphenyl)-ethyl]-cyclohexanol ($d_{20}$-venlafaxine)

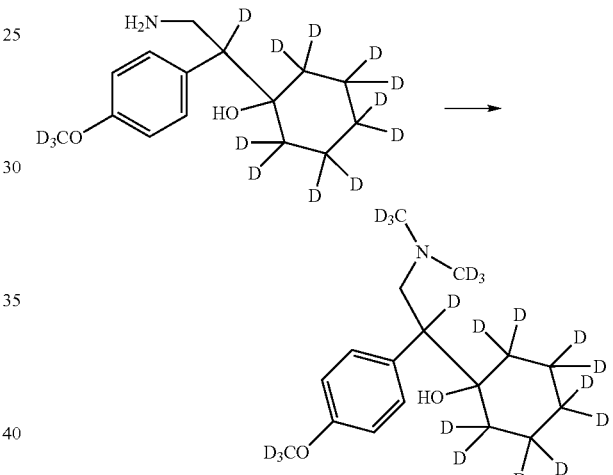

The title compound was prepared as in Example 8.

Yield (31%). $^1$H-NMR (CDCl$_3$) δ ppm: 2.33 (d, 1H, J=12.6 Hz), 3.30 (d, 1H, J=12.6 Hz), 6.81 (d, 2H, J=9.0 Hz), 7.05 (d, 2H, J=9.0 Hz). MS (m/z): 298 (M+1).

Example 13

In Vitro Liver Microsomal Stability Assay

Liver microsomal stability assays were conducted at 1 mg per mL liver microsome protein with an NADPH-generating system in 2% NaHCO$_3$ (2.2 mM NADPH, 25.6 mM glucose 6-phosphate, 6 units per mL glucose 6-phosphate dehydrogenase and 3.3 mM MgCl$_2$). Test compounds were prepared as solutions in 20% acetonitrile-water and added to the assay mixture (final assay concentration 5 microgram per mL) and incubated at 37° C. Final concentration of acetonitrile in the assay were <1%. Aliquots (50 μL) were taken out at times 0, 15, 30, 45, and 60 minutes, and diluted with ice cold acetonitrile (200 μL) to stop the reactions. Samples were centrifuged at 12000 RPM for 10 minutes to precipitate proteins. Supernatants were transferred to microcentrifuge tubes and stored for LC/MS/MS analysis of the degradation half-life of the test compounds. It has thus been found that the compounds of formula (1) according to the present invention that have been tested in this assay showed an increase of 10% or more in the degradation half-life, as compared to the non-isotopically enriched drug. For example, the degradation half-life of $d_3$-venlafaxine, $d_9$-venlafaxine, $d_{14}$-venlafaxine, and $d_{20}$-venlafaxine were increased by 50-300% as compared to non-isotopically enriched venlafaxine.

Example 14

In Vitro Metabolism Using Human Cytochrome $P_{450}$ Enzymes

The cytochrome P450 enzymes are expressed from the corresponding human cDNA using a baculovirus expression system (BD Biosciences). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula 1, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g. acetonitrile, 20% trichloroacetic acid, 94% acetonitrile/6% glacial acetic acid, 70% perchloric acid, 94% acetonitrile/6% glacial acetic acid) and centrifuged (10,000 g) for 3 minutes. The supernatant is analyzed by HPLC/MS/MS.

| Cytochrome $P_{450}$ | Standard |
| --- | --- |
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Pharmacology

The pharmacological profile of compounds of Formula 1 or the corresponding non-isotopically enriched compounds or standards or controls can be demonstrated as follows. The preferred exemplified compounds exhibit a $K_i$ value less than 1 micromolar, more preferably less than 500 nanomolar at the Serotonin transporter as determined using the scintillation proximity assay (SPA) described below. See WO 2005/060949. Furthermore, the preferred exemplified compounds selectively inhibit the Serotonin transporter relative to the Norepinephrine and dopamine transporters by a factor of at least five using such SPAs.

Example 15

Generation of Stable Cell Lines Expressing the Human Dopamine, Norepinephrine and Serotonin Transporters Standard molecular cloning techniques are used to generate stable cell-lines expressing the human Dopamine, Norepinephrine and Serotonin transporters. The polymerase chain reaction (PCR) is used in order to isolate and amplify each of the three full-length cDNAs from an appropriate cDNA library. PCR Primers for the following neurotransmitter transporters are designed using published sequence data. The PCR products are cloned into a mammalian expression vector, such as for example pcDNA3.1 (Invitrogen), using standard ligation techniques, followed by co-transfection of HEK293 cells using a commercially available lipofection reagent (Lipofectamine™-Invitrogen) following the manufacturer's protocol.

Human Dopamine transporter: GenBank M95167. Vandenbergh et al, *Molecular Brain Research* 1992, 15, 161-166, which is hereby incorporated by reference in its entirety.

Human Norepinephrine transporter: GenBank M65105. Pacholczyk et al, *Nature* 1991, 350, 350-354, which is hereby incorporated by reference in its entirety.

Human Serotonin transporter: GenBank L05568. Ramamoorthy et al, *Proceedings of the National Academy of Sciences of the USA* 1993, 90, 2542-2546, which is hereby incorporated by reference in its entirety.

Example 16

In Vitro SPA Binding Assay for the Norepinephrine Transporter

The assay is preformed according to the procedure described in Gobel et al, *Journal of Pharmacological and Toxicological Methods* 1999, 42(4), 237-244, which is hereby incorporated by reference in its entirety. Compound of Formula 1 or the corresponding non-isotopically enriched compounds are Serotonin/Norepinephrine reuptake inhibitors; $^3$H-nisoxetine binding to Norepinephrine re-uptake sites in a cell line transfected with DNA encoding human Norepinephrine transporter binding protein has been used to determine the affinity of ligands at the Norepinephrine transporter.

Membrane Preparation

Cell pastes from large scale production of HEK-293 cells expressing cloned human Norepinephrine transporters are homogenized in 4 volumes of 50 millimolar Tris-HCl containing 300 millimolar NaCl and 5 millimolar KCl, pH 7.4. The homogenate is centrifuged twice (40,000 g, 10 minutes, 4° C.) with pellet re-suspension in 4 volumes of Tris-HCl buffer containing the above reagents after the first spin, and 8 volumes after the second spin. The suspended homogenate is centrifuged (100 g, 10 minutes, 4° C.), the supernatant is kept and re-centrifuged (40,000 g, 20 minutes, 4° C.). The pellet is re-suspended in Tris-HCl buffer containing the above reagents along with 10% w/v sucrose and 0.1 millimolar phenylmethylsulfonyl fluoride (PMSF). The membrane preparation is stored in aliquots (1.0 milliliter) at −80° C. until required. The protein concentration of the membrane preparation is determined using a Bicinchoninic acid (BCA) protein assay reagent kit (available from Pierce).

[$^3$H]-Nisoxetine Binding Assay

Each well of a 96 well microtiter plate is set up to contain 50 microliters of 2 nanomolar [N-methyl-3H]-Nisoxetine hydrochloride (70-87 Ci/millimole, from NEN Life Science Products), 75 microliters Assay buffer (50 millimolar Tris-HCl pH 7.4 containing 300 millimolar NaCl and 5 millimolar KCl), 25 microliter of diluted compounds of Formula 1 or the corresponding non-isotopically enriched compounds, assay buffer (total binding) or 10 micromolar Desipramine HCl (non-specific binding), 50 microliter wheat germ agglutinin coated poly (vinyltoluene) (WGA PVT) SPA Beads (Amersham Biosciences RPNQ0001) (10 milligram/milliliter), 50 microliter membrane (0.2 milligram protein per milliliter).

The microtiter plates are incubated at room temperature for 10 hours prior to reading in a Trilux scintillation counter. The results are analyzed using an automatic spline-fitting program (Multicalc, Packard, Milton Keynes, UK) to provide $K_i$ values for each of the test compounds.

Example 17

In Vitro SPA Binding Assay for the Serotonin Transporter

The assay is preformed according to the procedure described in Ramamoorthy et al, *J. Biol. Chem.* 1998, 273(4), 2458-2466, which is hereby incorporated by reference in its entirety. The ability of a compound of Formula 1 or the corresponding non-isotopically enriched compound to compete with [$^3$H]-Citalopram for its binding sites on cloned human Serotonin transporter containing membranes has been used as a measure of test compound ability to block Serotonin uptake via its specific transporter.
Membrane Preparation Membrane preparation is essentially similar to that for the Norepinephrine transporter containing membranes as described above. The membrane preparation is stored in aliquots (1 milliliter) at −70° C. until required. The protein concentration of the membrane preparation is determined using a BCA protein assay reagent kit.
[$^3$H]-Citalopram Binding Assay Each well of a 96 well microtiter plate is set up to contain 50 microliters of 2 nanomolar [$^3$H]-Citalopram (60-86Ci/millimole, Amersham Biosciences), 75 microliters Assay buffer (50 millimolar Tris-HCl pH 7.4 containing 150 millimolar NaCl and 5 millimolar KCl), 25 microliters of diluted compounds of Formula 1 or the corresponding non-isotopically enriched compounds, assay buffer (total binding) or 100 micromolar Fluoxetine (non-specific binding), 50 microliters WGA PVT SPA Beads (40 milligram/milliliter), 50 microliters membrane preparation (0.4 milligram protein per milliliter). The microtiter plates are incubated at room temperature for 10 hours prior to reading in a Trilux scintillation counter. The results are analyzed using an automatic spline-fitting program (Multicalc, Packard, Milton Keynes, UK) to provide $K_i$ (nanomolar) values for each of the test compounds.

Example 18

In Vitro SPA Binding Assay for the Dopamine Transporter

The assay is preformed according to the procedure described in Ramamoorthy et al, *J. Biol. Chem.* 1998, 273(4), 2458-2466, which is hereby incorporated by reference in its entirety. The ability of a test compound to compete with [$^3$H]-WIN35,428 for its binding sites on human cell membranes containing cloned human dopamine transporter has been used as a measure of the ability of such test compounds to block Dopamine uptake via its specific transporter.
Membrane Preparation Is essentially the same as for membranes containing cloned human Serotonin transporter as described above.
[$^3$H]-WIN35,428 Binding Assay Each well of a 96 well microtiter plate is set up to contain 50 microliters of 4 nanomolar [$^3$H]-WIN35,428 (84-87 Ci/millimole, from NEN Life Science Products), 5 microliters Assay buffer (50 millimolar Tris-HCl pH 7.4 containing 150 millimolar NaCl and 5 millimolar KCl), 25 microliters of diluted compounds of Formula 1 or the corresponding non-isotopically enriched compounds, assay buffer (total binding) or 100 micromolar Nomifensine (non-specific binding), 50 microliters WGA PVT SPA Beads (10 milligram/milliliter), 50 microliters membrane preparation (0.2 milligram protein per milliliter). The microtiter plates are incubated at room temperature for 120 minutes prior to reading in a Trilux scintillation counter. The results are analyzed using an automatic spline-fitting program (Multicalc, Packard, Milton Keynes, UK) to provide $K_i$ values for each of the test compounds.

Example 19

In Vivo Assay for Behavioral Despair in Rats

The assay is performed according to the procedure described in Porsolt et al, *Archives Internationales de Pharmacodynamie et de Therapie,* 1977, 229(2), 327-336, which is hereby incorporated by reference in its entirety. After intraperitoneal administration of test compound in rats, animals are put in a cylinder containing water for 6 minutes. Immobility time is measured during the last 4 minutes. Diminished time of immobility is indicative of increased efficacy.

Although the invention has been described with reference to the above examples, it will be understood that modifications and variations are encompassed within the spirit and scope of the invention. Accordingly, the invention is limited only by the following claims.

REFERENCES CITED

The disclosures of each of the following references are incorporated by reference herein in their entireties.

Patent Documents

U.S. Pat. No. 4,069,346 Feb. 14, 1977 McCarty
U.S. Pat. No. 5,386,032 Jan. 31, 1995 Brandstrom
EP0654264 May 24, 1995 Thor
U.S. Pat. No. 5,846,514 Dec. 8, 1998 Foster
U.S. Pat. No. 6,221,335 Apr. 24, 2001 Foster
U.S. Pat. No. 6,333,342 Dec. 25, 2001 Foster
U.S. Pat. No. 6,334,997 Jan. 1, 2002 Foster
U.S. Pat. No. 6,342,507 Jan. 29, 2002 Foster
U.S. Pat. No. 6,476,058 Nov. 5, 2002 Foster
U.S. Pat. No. 6,503,921 Jan. 7, 2003 Naicker
U.S. Pat. No. 6,605,593 Aug. 12, 2003 Naicker
U.S. Pat. No. 6,613,739 Sep. 2, 2003 Naicker
U.S. Pat. No. 6,710,053 Mar. 23, 2004 Naicker
U.S. Pat. No. 6,818,200 Nov. 16, 2004 Foster
U.S. Pat. No. 6,884,429 Apr. 26, 2005 Koziak Other References Altermatt, *Cancer* 1988, 62(3), 462-466, "Heavy water delays growth of human carcinoma in nude-mice".
Altermatt, *International Journal of Cancer* 1990, 45(3), 475-480, "Heavy-Water Enhances the Antineoplastic Effect of 5-Fluoro-Uracil and Bleomycin in Nude Mice Bearing Human Carcinoma".
Baldwin, *International Journal of Neuropsychopharmacology* 2005, 8(2), 293-302, "Evidence-based pharmacotherapy of Generalized Anxiety Disorder".
Baselt, *Disposition of Toxic Drugs and Chemicals in Man,* 2004, 7th Edition.
Bassapa et al, *Bioorganic & Medicinal Chemistry Letters* 2004, 14, 3279-3281, "Simple and efficient method for the synthesis of 1-[2-dimethylamino-1(4-methoxy-phenyl)-ethyl]-cyclohexanol hydrochloride: (±) venlafaxine racemic mixtures".

Browne, *Synthesis and Applications of isotopically Labelled Compounds, Proceedings of the International Symposium*, 7th, Dresden, Germany, Jun. 18-22, 2000, 519-532, "Stable Isotopes in Pharmaceutical Research and Development"

Browne, *Pharmacochemistry Library*, 1997, 26, "Stable Isotopes in Pharmaceutical Research".

Browne, *Pharmacochemistry Library*, 1997, 26, 13-18, "Isotope effect: implications for pharmaceutical investigations".

Browne, *Clinical Pharmacology & Therapeutics*, 1981, 29(4), 511-15, "Kinetic equivalence of stable-isotope-labeled and unlabeled phenyloin".

Browne, *Journal of Clinical Pharmacology* 1982, 22(7), 309-15, "Pharmacokinetic Equivalence of Stable-Isotope-Labeled and Unlabeled Drugs. Phenobarbital in Man".

Browne, *Synth. Appl. Isot. Labeled Compd., Proc. Int. Symp.* 1983, Meeting Date 1982, 343-8, "Applications of Stable Isotope Tracer Methods to Human Drug Interaction Studies".

Browne, *Therapeutic Drug Monitoring* 1984, 6(1), 3-9, "Applications of Stable Isotope Methods to Studying the Clinical Pharmacology of Antiepileptic Drugs in Newborns, Infants, Children, and Adolescents".

Chavan et al, *Tetrahedron Letters* 2004, 45, 7291-7295, "An efficient and green protocol for the preparation of cycloalkanols: a practical synthesis of venlafaxine".

Davies et al, *Journal of the Chemical Society, Abstracts* 1945, 352-354, Novel Pyrimidine Synthesis. II. 4-Amino-5-arylpyrimidines".

Ding et al *Journal of Neurochemistry* 1995, 65(2), 682-690, "Mechanistic Positron Emission Tomography Studies of 6-[$^{18}$F]Fluorodopamine in Living Baboon Heart: Selective Imaging and Control of Radiotracer Metabolism Using the Deuterium Isotope Effect".

Foster, *Trends in Pharmacological Sciences* 1984, 5(12), 524-527, "Deuterium Isotope Effects in Studies of Drug Metabolism".

Garland, *Synth. Appl. Isot. Labeled Compd. Proc. Int. Symp.* 2$^{nd}$, 1986, Meeting Date 1985, 283-284, "The Use of Deuterated Analogs of Drugs as Medicinal Agents: Introduction and Report of Discussion".

Gobel et al, *Journal of Pharmacological and Toxicological Methods* 1999, 42(4), 237-244, "Development of Scintillation-Proximity Assays for Alpha Adrenoceptors".

Goeringer, *Journal of Forensic Sciences* 2000, 45(3), 633-648, "Postmortem Forensic Toxicology of Selective Serotonin Reuptake Inhibitors: a Review of Pharmacology and Report of 168 Cases".

Katzman, *Expert Review of Neurotherapeutics*, 2005, 5(1), 129-139, "Pharmacotherapy of post-traumatic stress disorder: A family practitioner's guide to management of the disease".

Kaufman, *Phys. Rev.* 1954, 93, 1337-1344, "The Natural Distribution of Tritium".

Ko et al *British Journal of Clinical Pharmacology* 2000, 49(4), 343-351, "In Vitro Inhibition of the Cytochrome P450 (CYP450) System by the Antiplatelet Drug Ticlopidine: Potent Effect on CYP2C19 and CYP2D6".

Kritchevsky, *Annals of the New York Academy of Science* 1960, vol. 84, article 16, "Deuterium Isotope Effects in Chemistry and Biology".

Kushner, *Can. J. Physiol. Pharmacol.* 1999, 77, 79-88, "Pharmacological Uses and Perspectives of Heavy Water and Deuterated Compounds".

Lamprect, *European Journal of Cell Biology* 1990, 51(2), 303-312, "Mitosis Arrested By Deuterium Oxide—Light Microscopic, Immunofluorescence and Ultrastructural Characterization".

Lessard et al, *Pharmacogenetics* 1999, 9(4), 435-443, "Influence of CYP2D6 activity on the disposition and cardiovascular toxicity of the antidepressant agent venlafaxine in humans".

Lewis, *J. Am. Chem. Soc.* 1968, 90, 4337, "The influence of Tunneling on the Relation Between Tritium and Deuterium Isotope Effects. The Exchange of 2-Nitropropane-2-T".

Li et al *Rapid Communications in Mass Spectrometry* 2005, 19(14), 1943-1950, "Simultaneously Quantifying Parent Drugs and Screening for Metabolites in Plasma Pharmacokinetic Samples Using Selected Reaction Monitoring Information-Dependent Acquisition on a Qtrap Instrument".

March, *Advanced Organic Chemistry* 1992, 4th edition, 226-230.

Morton et al, *Annals of Pharmacotherapy* 1995, 29(4), 387-395, "Venlafaxine: a structurally unique and novel antidepressant".

Ouk et al *Green Chemistry*, 2002, 4(5), 431-435, "Dimethyl carbonate and phenols to alkyl aryl ethers via clean synthesis".

Pacher, *Current Medicinal Chemistry* 2004, 11(7), 925-943, "Trends in the development of new antidepressants. Is there a light at the end of the tunnel?".

Pacher et al, *Current Pharmaceutical Design* 2004, 10(20), 2463-2475, "Cardiovascular side effects of new antidepressants and antipsychotics: New drugs, old concerns?".

Pacholczyk et al, *Nature* 1991, 350, 350-354, "Expression Cloning of a Cocaine- and Antidepressant-Sensitive Human Noradrenaline Transporter".

Phelps et al, *Annals of Pharmacotherapy* 2005, 39(1), 136-140, "The role of venlaxafine in the treatment of obsessive-compulsive disorder".

Physicians Desk Reference, 2003.

Porsolt et al, *Archives Internationales de Pharmacodynamie et de Therapie*, 1977, 229(2), 327-336, "Behavioral Despair in Mice: a Primary Screening Test for Antidepressants".

Pohl, *Drug Metabolism Reviews* 1985 (Volume Date 1984), 15(7), 1335-1351, "Determination of Toxic Pathways of Metabolism by Deuterium Substitution".

Preskorn et al, *Handbook of Experimental Pharmacology. Antidepressants: Past, Present and Future*, 2004, Volume 157.

Raggi, *Current Topics in Medicinal Chemistry* 2003, 3, 203-220, "New Trends in the Treatment of Depression: Pharmacological Profile of Selective Serotonin Reuptake Inhibitors".

Ramamoorthy et al, *J. Biol. Chem.* 1998, 273(4), 2458-2466, "Phosphorylation and Regulation of Antidepressant-Sensitive Serotonin Transporters".

Ramamoorthy et al, *Proceedings of the National Academy of Sciences of the USA* 1993, 90, 2542-2546 "Antidepressant- and Cocaine-Sensitive Human Serotonin Transporter: Molecular Cloning, Expression, and Chromosomal Localization".

Reis et al, *Therapeutic Drug Monitoring* 2002, 24, 545-553, "Therapeutic Drug Monitoring of Racemic Venlafaxine and Its Main Metabolites in an Everyday Clinical Setting".

Roecker, *J. Am. Chem. Soc.* 1987, 109, 746, "Hydride Transfer in the Oxidation of Alcohols by [(bpy)$_2$(py)Ru(O)]$^{2+}$. A $k_H/k_D$ Kinetic Isotope Effect of 50".

Schroeter, *European Journal of Cell Biology* 1992, 58(2), 365-370, "Deuterium Oxide Arrests the Cell-Cycle of PTK2 Cells During Interphase".

Sicat et al, *Pharmacotherapy* 2004, 24(1), 79-93, "Nonhormonal alternatives for the treatment of hot flashes".

Silverstone, *Journal of Clinical Psychiatry* 2004, 65(Suppl. 17), 19-28, "Qualitative Review of SNRIs in Anxiety".

Tolonen, *European Journal of Pharmaceutical Sciences* 2005, 25, 155-162, "A Simple Method for Differentiation of Monoisotopic Drug Metabolites with Hydrogen-Deuterium Exchange Liquid Chromatography/Electrospray Mass Spectrometry".

Thomson, *International Series of Monographs on Pure and Applied Biology, Modern trends in Physiological Sciences,* 1963, "Biological Effects of Deuterium".

Urey, *Phys. Rev.* 1932, 39, 164 "A Hydrogen Isotope of Mass 2".

Vandenbergh et al, *Molecular Brain Research* 1992, 15, 161-166, "A Human Dopamine Transporter cDNA Predicts Reduced Glycosylation, Displays a Novel Repetitive Element and Provides Racially-Dimorphic TaqIRFLPs".

Yardley et al, *Journal of Medicinal Chemistry* 1990, 33(10), 2899-2905, "2-Phenyl-2-(1-hydroxycycloalkyl)ethylamine Derivatives: Synthesis and Antidepressant Activity".

What is claimed is:

1. A method of treating a mammal suffering from a disease, condition, or disorder selected from the group consisting of a psychotropic disorder, an anxiety disorder, a generalized anxiety disorder, depression, a post-traumatic stress disorder, an obsessive-compulsive disorder, a panic disorder, a hot flash, senile dementia, migraine, hepatopulmonary syndrome, chronic pain, nociceptive pain, neuropathic pain, painful diabetic retinopathy, bipolar depression, obstructive sleep apnea, a psychiatric disorder, a premenstrual dysphoric disorder, a social phobia, a social anxiety disorder, urinary incontinence, anorexia, bulimia nervosa, obesity, ischemia, head injury, calcium overload in brain cells, drug dependence, and premature ejaculation comprising administering to said mammal a therapeutically effective amount of a compound having structural Formula 1

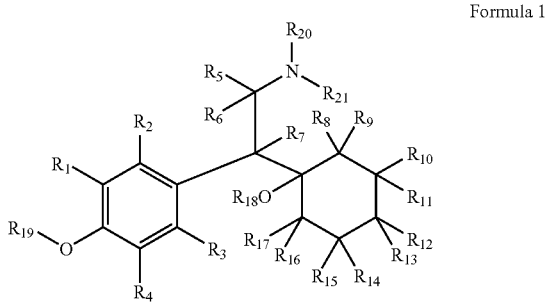

Formula 1 or a pharmaceutically acceptable salt thereof, wherein:

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from the group consisting of hydrogen and deuterium;

$R_{19}$, $R_{20}$, and $R_{21}$ are independently selected from the group consisting of —CH$_3$ and —CD$_3$;

provided that said compound of Formula 1 contains at least three deuterium atoms; and provided that deuterium enrichment in said compound of Formula 1 is at least about 1%.

2. The method of claim 1, wherein said disease, condition, or disorder is depression.

3. The method of claim 1, wherein the compound of Formula I affects decreased inter-individual variation in plasma levels of said compound or a metabolite thereof as compared to the non-isotopically enriched compound.

4. The method of claim 1, wherein the compound of Formula I affects increased average plasma levels of said compound per dosage unit thereof as compared to the non-isotopically enriched compound.

5. The method of claim 1, wherein the compound of Formula I affects decreased average plasma levels of at least one metabolite of said compound per dosage unit thereof as compared to the non-isotopically enriched compound.

6. The method of claim 1, wherein the compound of Formula I affects a decreased metabolism by at least one polymorphically-expressed cytochrome P$_{450}$ isoform in mammalian subjects per dosage unit thereof as compared to the non-isotopically enriched compound.

7. The method of claim 6, wherein said cytochrome P$_{450}$ isoform is selected from the group consisting of CYP2C8, CYP2C9, CYP2C19, and CYP2D6.

8. The method of claim 1, wherein the compound of Formula I affects a decreased inhibition of at least one cytochrome P$_{450}$ isoform in mammalian subjects per dosage unit thereof as compared to the non-isotopically enriched compound.

9. The method of claim 8, wherein said cytochrome P$_{450}$ isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4×1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

10. The method of claim 1, wherein the compound of Formula I elicits an improved clinical effect during the treatment in said mammal per dosage unit thereof as compared to the non-isotopically enriched compound.

11. The method of claim 10, wherein the said improved clinical effect comprises an effect selected from the group consisting of accelerated rate of healing, accelerated rate of symptom relief, improved patient compliance, and reduced substance abuse withdrawal symptomology during the treatment.

12. A method of treating a mammal for a drug addiction comprising co-administering a first component and a second component, wherein said first component comprises a therapeutically effective amount of a compound of Formula 1, and said second component comprises a therapeutically effective amount of an opioid antagonist, said compound having structural Formula 1

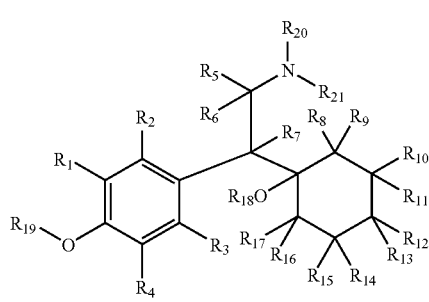

Formula 1 or a pharmaceutically acceptable salt thereof, wherein:
$R_1, R_2, R_3, R_4, R_5, R_6, R_7, R_8, R_9, R_{10}, R_{11}, R_{12}, R_{13}, R_{14}, R_{15}, R_{16}, R_{17}$, and $R_{18}$ are independently selected from the group consisting of hydrogen and deuterium;
$R_{19}, R_{20}$, and $R_{21}$ are independently selected from the group consisting of —CH$_3$ and —CD$_3$;
provided that said compound of Formula 1 contains at least three deuterium atoms; and
provided that deuterium enrichment in said compound of Formula 1 is at least about 1%.

13. The method of claim 12, wherein said opioid antagonist is selected from the group consisting of nalmefene, naltrexone, and naloxone.

14. The method of claim 12, wherein said drug addiction is selected from the group consisting of tobacco addiction, alcohol addiction, marijuana addiction, and cocaine addiction.

15. The method of claim 12, wherein said first component elicits an improved clinical effect for the treatment of a drug addiction, as compared to the non-isotopically enriched analog of the first component.

16. The method of claim 15, wherein said improved clinical effect is selected from the group consisting of an accelerated rate of healing, an accelerated rate of symptom relief, improved patient compliance, and reduced substance abuse withdrawal symptomatology during the treatment.

17. The method of claim 1, wherein said compound of Formula 1 has the structural formula:

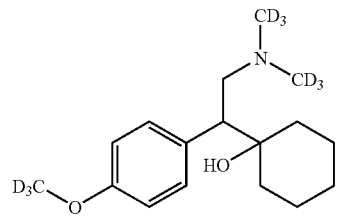

or a pharmaceutically acceptable salt thereof.

18. The method of claim 17, wherein said compound of Formula 1 is a mixture of about 90% or more by weight of the (+)-enantiomer and about 10% or less by weight of the (−)-enantiomer.

19. The method of claim 17, wherein said compound of Formula 1 is a mixture of about 90% or more by weight of the (−)-enantiomer and about 10% or less by weight of the (+)-enantiomer.

20. The method of claim 17, wherein said compound of Formula 1 is a hydrochloride salt.

21. The method of claim 20, wherein said hydrochloride salt is a mixture of about 90% or more by weight of the (+)-enantiomer and about 10% or less by weight of the (−)-enantiomer.

22. The method of claim 20, wherein said hydrochloride salt is a mixture of about 90% or more by weight of the (−)-enantiomer and about 10% or less by weight of the (+)-enantiomer.

23. The method of claim 12, wherein said compound of Formula 1 has the structural formula:

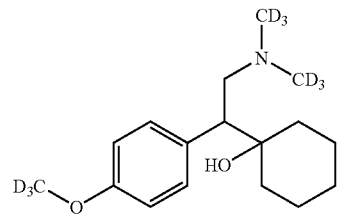

or a pharmaceutically acceptable salt thereof.

24. The method of claim 23, wherein said compound of Formula 1 is a mixture of about 90% or more by weight of the (+)-enantiomer and about 10% or less by weight of the (−)-enantiomer.

25. The method of claim 23, wherein said compound of Formula 1 is a mixture of about 90% or more by weight of the (−)-enantiomer and about 10% or less by weight of the (+)-enantiomer.

26. The method of claim 23, wherein said compound of Formula 1 is a hydrochloride salt.

27. The method of claim 26, wherein said hydrochloride salt is a mixture of about 90% or more by weight of the (+)-enantiomer and about 10% or less by weight of the (−)-enantiomer.

28. The method of claim 26, wherein said hydrochloride salt is a mixture of about 90% or more by weight of the (−)-enantiomer and about 10% or less by weight of the (+)-enantiomer.

* * * * *